(12) United States Patent
Peng

(10) Patent No.: US 9,758,782 B2
(45) Date of Patent: Sep. 12, 2017

(54) INHIBITION OF MICRORNA FOR TREATMENT OF SEPSIS

(71) Applicant: LONDON HEALTH SCIENCES CENTRE RESEARCH INC., London (CA)

(72) Inventor: Tianqing Peng, London (CA)

(73) Assignee: LONDON HEALTH SCIENCES CENTRE RESEARCH INC., London, Ontario (CA)

( * ) Notice: Subject to any disclaimer, the term of this patent is extended or adjusted under 35 U.S.C. 154(b) by 0 days.

(21) Appl. No.: 14/901,549

(22) PCT Filed: Jun. 25, 2014

(86) PCT No.: PCT/CA2014/000525
§ 371 (c)(1),
(2) Date: Dec. 28, 2015

(87) PCT Pub. No.: WO2014/205551
PCT Pub. Date: Dec. 31, 2014

(65) Prior Publication Data
US 2016/0145616 A1 May 26, 2016

Related U.S. Application Data

(60) Provisional application No. 61/840,981, filed on Jun. 28, 2013.

(51) Int. Cl.
| | | |
|---|---|---|
| *A61K 31/715* | (2006.01) | |
| *C12N 15/11* | (2006.01) | |
| *C07H 21/04* | (2006.01) | |
| *C07H 21/02* | (2006.01) | |
| *C12N 15/113* | (2010.01) | |
| *A61K 31/7088* | (2006.01) | |

(52) U.S. Cl.
CPC ........ *C12N 15/113* (2013.01); *A61K 31/7088* (2013.01); *C12N 2310/113* (2013.01); *C12N 2320/30* (2013.01)

(58) Field of Classification Search
None
See application file for complete search history.

(56) References Cited

U.S. PATENT DOCUMENTS

| | | | | |
|---|---|---|---|---|
| 2008/0300211 A1* | 12/2008 | Baltimore | ............ | C12N 15/113 514/44 A |
| 2010/0317713 A1* | 12/2010 | Olson | ................ | A01K 67/0275 514/44 A |
| 2011/0190372 A1 | 8/2011 | Tomic-Canic | | |
| 2014/0294943 A1* | 10/2014 | Juo | ...................... | C12N 15/113 424/450 |

OTHER PUBLICATIONS

Vasques-Novoa (Circulation 126:A14713, 2012).*
Pasquinelli (Nature Reviews Genetics 13:271-2082, 2012).*
Sun, Y. et al., "Targeting of microRNA-142-3p in dendritic cells regulates endotoxin-induced mortality." Blood, Jun. 9, 2011, pp. 6172-6183.
Zhu, H. et al., "MicroRNA-195 promotes palmitate-induced apoptosis in cardiomyocytes by down-regulating Sirt1." cardiovascular Research, Oct. 1, 2011, pp. 75-84.
Wang, H. et al., "Evidence for serum miR-15a and miR-16 levels as biomarkers that distinguish sepsis from systemic inflammatory response syndrome in human subjects." Clinical Chemistry in Laboratory Medicine, Feb. 11, 2012, pp. 14223-1428.
Wu, S.-C. et al. Profiling circulating microRNA expression in experimental sepsis using cecal ligation and puncture. PloS One [online] Oct. 2013. Retrieved from the Internet: <URL:http://www.plosone.org/article/info%3Adoi%2F10.1371%2Fjournal.pone.0077936>.
International Search Report dated Oct. 8, 2014 for PCT/CA2014/000525.

* cited by examiner

*Primary Examiner* — Richard Schnizer
(74) *Attorney, Agent, or Firm* — Knobbe, Martens, Olson & Bear, LLP

(57) ABSTRACT

A method of treating sepsis comprises administering an agent that inhibits the activity of an miRNA that is upregulated in sepsis.

7 Claims, 12 Drawing Sheets

Sham   Control plasmid   miR-195 inhibitor
LPS

INHIBITION OF MICRORNA FOR TREATMENT OF SEPSIS

CROSS REFERENCE TO RELATED APPLICATIONS

This application is the U.S. National Phase of International Application No. PCT/CA2014/000525, filed Jun. 25, 2014, designating the U.S. and published in English as WO 2014/205551 on Dec. 31, 2014 which claims the benefit of U.S. Provisional Patent Application No. 61/840,981, filed Jun. 28, 2013. Any and all applications for which a foreign or domestic priority claim is identified here or in the Application Data Sheet as filed with the present application are hereby incorporated by reference under 37 CFR 1.57.

FIELD OF THE INVENTION

The present invention relates to miRNA. More specifically, the present invention is concerned with methods of treating sepsis and other disorders through use of miRNA inhibitors.

BACKGROUND OF THE INVENTION

MicroRNAs (miRNAs) are small non-coding RNA molecules, on average 22 nucleotides long, that function in transcriptional and post-transcriptional regulation of gene expression. Encoded by eukaryotic nuclear DNA, miRNAs function via base-pairing with complementary sequences within mRNA molecules, usually resulting in gene silencing via translational repression or target degradation. The human genome may encode over 1000 miRNAs, which may target about 60% of mammalian genes and are abundant in many human cell types. Aberrant expression of miRNAs has been implicated in numerous disease states, and miRNA-based therapies are under investigation.

For example, Zhu et al. (Cardiovascular Research, 2011, 92:75-84) found that microRNA-195 (miR-195) promotes palmitate-induced apoptosis in cardiomyocytes by down-regulating Sirt1.

Wang et al. (PLoS ONE, 2012, 7(6):e38885) found that serum miRNA signatures can predict mortality in sepsis patients.

There remains a need to identify one or a combination of miRNAs that can be specifically targeted to treat or prevent various disease states.

SUMMARY

The present invention relates, in aspects, to methods of treating sepsis or other related disorders through use of miRNA inhibitors that target and/or inhibit the activity of miRNAs of the miR-15 family. In this way, the miRNA inhibitors are, in an aspect, useful in the treatment of diseases, disorders, or conditions that involve upregulation of miR-15 family members, such as, for example, sepsis.

In an aspect, there is provided a method of treating sepsis, comprising administering an agent that inhibits the activity of an miRNA that is upregulated in sepsis.

In an aspect, the miRNA is a member of the miRNA-15 family.

In an aspect, the miRNA is at least one of mir-15a, mir-15b, miR-16-1, miR-16-2, miR-195, mir-322/424, and miR-497.

In an aspect, the miRNA is miR-195.

In an aspect, the agent protects organ function.

In an aspect, the organ function is at least one of liver function, lung function, kidney function, and microvasculature function.

In an aspect, the agent reduces apoptosis.

In an aspect, the agent reduces apoptosis in at least one of endothelial cells, liver cells, kidney cells, and immune cells.

In an aspect, the immune cells are macrophages.

In an aspect, the agent reduces an inflammatory response.

In an aspect, the inflammatory response is in at least one of a liver, lung, kidney, and microvasculature.

In an aspect, the sepsis is lipopolysaccharide-induced sepsis or feces-induced sepsis.

In accordance with another aspect, there is provided a method of protecting organ function, comprising administering an agent that inhibits the activity of an miRNA of the miRNA-15 family.

In an aspect, the miRNA is at least one of mir-15a, mir-15b, miR-16-1, miR-16-2, miR-195, mir-322/424, and miR-497.

In an aspect, the organ function is at least one of liver function, lung function, kidney function, and microvasculature function.

In accordance with another aspect, there is provided a method of reducing apoptosis, comprising administering an agent that inhibits the activity of an miRNA of the miRNA-15 family.

In an aspect, the miRNA is at least one of mir-15a, mir-15b, miR-16-1, miR-16-2, miR-195, mir-322/424, and miR-497.

In an aspect, the agent reduces apoptosis in at least one of endothelial cells, liver cells, kidney cells, and immune cells.

In an aspect, the immune cells are macrophages.

In accordance with another aspect, there is provided a method of reducing an inflammatory response, comprising administering an agent that inhibits the activity of an miRNA of the miRNA-15 family.

In an aspect, the miRNA is at least one of mir-15a, mir-15b, miR-16-1, miR-16-2, miR-195, mir-322/424, and miR-497.

In an aspect, the inflammatory response is in at least one of a liver, lung, kidney, and microvasculature.

In an aspect, the agent is a locked nucleic acid (LNA) oligo, a Morpholino oligo, a 2'-O-methyl RNA oligo, an antagomir, a steric-blocking oligo that inhibits miRNA maturation, or a steric-blocking oligo that blocks the miRNA target site of an mRNA transcript.

In accordance with another aspect, there is provided a method of treating sepsis, comprising administering an agent that enhances the activity of a gene target of an miRNA that is upregulated in sepsis.

In accordance with another aspect, there is provided a use of an agent that inhibits the activity of an miRNA that is upregulated in sepsis for treatment of sepsis.

In an aspect, the miRNA is a member of the miRNA-15 family.

In an aspect, the miRNA is at least one of mir-15a, mir-15b, miR-16-1, miR-16-2, miR-195, mir-322/424, and miR-497.

In an aspect, the miRNA is miR-195.

In an aspect, the use is for protecting organ function.

In an aspect, the organ function is at least one of liver function, lung function, kidney function, and microvasculature function.

In an aspect, the use is for reducing apoptosis.

In an aspect, the use is for reducing apoptosis in at least one of endothelial cells, liver cells, kidney cells, and immune cells.

In an aspect, the immune cells are macrophages.

In an aspect, the use is for reducing an inflammatory response.

In an aspect, the inflammatory response is in at least one of a liver, lung, kidney, and microvasculature.

In an aspect, the sepsis is lipopolysaccharide-induced sepsis or feces-induced sepsis.

In accordance with another aspect, there us provided a use of an agent that inhibits the activity of an miRNA of the miRNA-15 family for protecting organ function.

In an aspect, the miRNA is at least one of mir-15a, mir-15b, miR-16-1, miR-16-2, miR-195, mir-322/424, and miR-497.

In an aspect, the organ function is at least one of liver function, lung function, kidney function, and microvasculature function.

In accordance with another aspect, there is provided a use of an agent that inhibits the activity of an miRNA of the miRNA-15 family for reducing apoptosis.

In an aspect, the miRNA is at least one of mir-15a, mir-15b, miR-16-1, miR-16-2, miR-195, mir-322/424, and miR-497.

In an aspect, the use is for reducing apoptosis in at least one of endothelial cells, liver cells, kidney cells, and immune cells.

In an aspect, the immune cells are macrophages.

In accordance with another aspect, there is provided a use of an agent that inhibits the activity of an miRNA of the miRNA-15 family for reducing an inflammatory response.

In an aspect, the miRNA is at least one of mir-15a, mir-15b, miR-16-1, miR-16-2, miR-195, mir-322/424, and miR-497.

In an aspect, the inflammatory response is in at least one of a liver, lung, kidney, and microvasculature.

In an aspect, the agent is a locked nucleic acid (LNA) oligo, a Morpholino oligo, a 2'-O-methyl RNA oligo, an antagomir, a steric-blocking oligo that inhibits miRNA maturation, or a steric-blocking oligo that blocks the miRNA target site of an mRNA transcript.

In accordance with another aspect, there is provided a use of an agent that enhances the activity of a gene target of an miRNA that is upregulated in sepsis for treatment of sepsis.

In accordance with another aspect, there is provided a composition comprising an agent that inhibits the activity of an miRNA that is upregulated in sepsis for use in treatment of sepsis.

In an aspect, the miRNA is a member of the miRNA-15 family.

In an aspect, the miRNA is at least one of mir-15a, mir-15b, miR-16-1, miR-16-2, miR-195, mir-322/424, and miR-497.

In an aspect, the miRNA is miR-195.

In an aspect, the agent is for use in protecting organ function.

In an aspect, the organ function is at least one of liver function, lung function, kidney function, and microvasculature function.

In an aspect, the agent is for use in reducing apoptosis.

In an aspect, the agent is for use in reducing apoptosis in at least one of endothelial cells, liver cells, kidney cells, and immune cells.

In an aspect, the immune cells are macrophages.

In an aspect, the agent is for use in reducing an inflammatory response.

In an aspect, the inflammatory response is in at least one of a liver, lung, kidney, and microvasculature.

In an aspect, the sepsis is lipopolysaccharide-induced sepsis or feces-induced sepsis.

In accordance with another aspect, there is provided a composition comprising an agent that inhibits the activity of an miRNA of the miRNA-15 family for use in protecting organ function.

In an aspect, the miRNA is at least one of mir-15a, mir-15b, miR-16-1, miR-16-2, miR-195, mir-322/424, and miR-497.

In an aspect, the organ function is at least one of liver function, lung function, kidney function, and microvasculature function.

In accordance with another aspect, there is provided a composition comprising an agent that inhibits the activity of an miRNA of the miRNA-15 family for use in reducing apoptosis.

In an aspect, the miRNA is at least one of mir-15a, mir-15b, miR-16-1, miR-16-2, miR-195, mir-322/424, and miR-497.

In an aspect, the composition is for use in reducing apoptosis in at least one of endothelial cells, liver cells, kidney cells, and immune cells.

In an aspect, the immune cells are macrophages.

In accordance with another aspect, there is provided a composition comprising an agent that inhibits the activity of an miRNA of the miRNA-15 family for use in reducing an inflammatory response.

In an aspect, the miRNA is at least one of mir-15a, mir-15b, miR-16-1, miR-16-2, miR-195, mir-322/424, and miR-497.

In an aspect, the inflammatory response is in at least one of a liver, lung, kidney, and microvasculature.

In an aspect, the agent is a locked nucleic acid (LNA) oligo, a Morpholino oligo, a 2'-O-methyl RNA oligo, an antagomir, a steric-blocking oligo that inhibits miRNA maturation, or a steric-blocking oligo that blocks the miRNA target site of an mRNA transcript.

In accordance with another aspect, there is provided a composition comprising an agent that enhances the activity of a gene target of an miRNA that is upregulated in sepsis for use in treatment of sepsis.

Other features and advantages of the present invention will become apparent from the following detailed description. It should be understood, however, that the detailed description and the specific examples while indicating aspects of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which:

FIGS. 11A, 11B, 110, 11D, 11E, and 11F show the therapeutic effects of miR-195 inhibition on apoptosis, inflammation and organ dysfunction in a mouse model of LPS-induced sepsis.

DETAILED DESCRIPTION OF CERTAIN EMBODIMENTS OF THE INVENTION

Figure 1A:
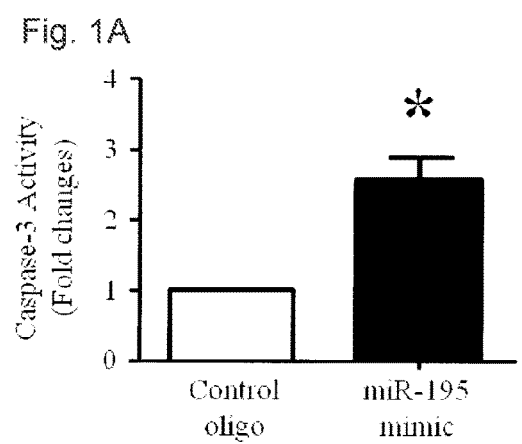
FIGS. 1A and 1B show that upregulation of miR-195 is sufficient to induce apoptosis in endothelial cells.

The present invention is directed to agents that bind to and/or interact with miRNA sequences that are upregulated in sepsis or other disorders as compared to their normal levels absent these disorders. Accordingly, these agents find use in treating disorders such as sepsis and in protecting organ function, reducing apoptosis, and reducing inflammatory responses. The specific miRNAs targeted by the agents described herein belong to, for example, the miRNA-15 family, such as mir-15a, mir-15b, miR-16-1, miR-16-2, miR-195, mir-322/424, and miR-497.

Unless defined otherwise, technical and scientific terms used herein have the same meaning as commonly understood by one of ordinary skill in the art to which this invention belongs. See, e.g. Singleton et al., Dictionary of Microbiology and Molecular Biology 2nd ed., J. Wiley & Sons (New York, N.Y. 1994); Sambrook et al., Molecular Cloning. A Laboratory Manual, Cold Springs Harbor Press (Cold Springs Harbor, N.Y. 1989), each of which are incorporated herein by reference. For the purposes of the present invention, the following terms are defined below.

As used herein, the term "miRNA" refers to microRNA molecules, which are small (around 22 nucleotides), non-coding RNA molecules that regulate gene expression post-transcriptionally by binding to mRNA sequences and targeting them for degradation. Specific miRNAs are named with the prefix "mir" followed by a dash and a number. "mir-" refers to pre-miRNA, whereas "miR-" refers to the mature form. For example, members of the miRNA-15 family include mir-15a, mir-15b, miR-16-1, miR-16-2, miR-195, mir-322/424, and miR-497.

"Variants" of the sequences described herein are biologically active sequences that have a nucleotide sequence that differs from the sequence of a native or wild-type sequence (or the complement thereof), by virtue of an insertion, deletion, modification and/or substitution of one or more nucleotides within the native sequence. Such variants generally have less than 100% sequence identity with a native sequence or its complement. Ordinarily, however, a biologically active variant will have a nucleotide sequence with at least about 70% sequence identity with the sequence or complement of a corresponding naturally occurring sequence, typically at least about 75%, more typically at least about 80%, even more typically at least about 85%, even more typically at least about 90%, and even more typically of at least about 95%, 96%, 97%, 98%, or 99% sequence identity. The variants nucleotide fragments of any length that retain a biological activity of the corresponding native sequence. Variants also include sequences wherein one or more nucleotides are added at the 5' or 3' end of, or within, a native sequence or its complement. Variants also include sequences where a number of nucleotides are deleted and optionally substituted by one or more different nucleotides.

"Percent sequence identity" is defined herein as the percentage of nucleotides or amino acid residues in the candidate sequence that are identical with the nucleotides or residues in the sequence of interest after aligning the sequences and introducing gaps, if necessary, to achieve the maximum percent sequence identity, and not considering any conservative substitutions as part of the sequence identity. None of 5', 3', or internal extensions, deletions or insertions into the candidate sequence shall be construed as affecting sequence identity or homology. Methods and computer programs for the alignment are well known in the art, such as "BLAST".

"Active" or "activity" for the purposes herein refers to a biological activity of a native or naturally-occurring miRNA, miRNA inhibitor, or miRNA target sequence, wherein "biological" activity refers to a biological function (either inhibitory or stimulatory) caused by a native or naturally-occurring miRNA, miRNA inhibitor, or miRNA target sequence.

Thus, "biologically active" or "biological activity" when used in conjunction with "miRNA," "miRNA inhibitor," or "miRNA target sequence" refers to a nucleotide sequence that exhibits or shares an effector function of the native miRNA, miRNA inhibitor, or miRNA target sequence. For example, miRNA inhibitors or agents that inhibit the activity of an miRNA have the biological activity of inhibiting the repressive activity of a specific miRNA sequence. Likewise, miRNA sequences typically have the biological activity of repressing translation of specific mRNA sequences and thereby inhibiting gene expression.

"Biologically active" or "biological activity" when used in conjunction with variant sequences means that the variant sequences exhibit or share an effector function of the parent sequence. The biological activity of the variant sequence may be increased, decreased, or at the same level as compared with the parent sequence.

The terms "inhibit" or "inhibitory" mean that a function or activity of an miRNA is decreased, limited, blocked, or neutralized. These terms encompass a complete or partial inhibition in miRNA function or activity, including the binding of a specific miRNA to its target mRNA.

An "miRNA target sequence" is an mRNA molecule to which a specific miRNA binds and inhibits. For example, the miRNA-15 family may target and repress important anti-apoptotic protein expression. These proteins include, but are not limited to, BCL-2, Sirt1, Pim-1, etc. Down-regulation of anti-apoptotic proteins will promote apoptotic cell death, which significantly contributes to sepsis-associated organ dysfunctions, leading to death. Thus, inhibition of members of the miR-15 family may prevent apoptosis and multiple organ dysfunctions in sepsis.

"Isolated" refers to a molecule that has been purified from its source or has been prepared by recombinant or synthetic methods and purified. Purified nucleotides are substantially free of other nucleotides or bases.

"Substantially free" herein means less than about 5%, typically less than about 2%, more typically less than about 1%, even more typically less than about 0.5%, most typically less than about 0.1% contamination with other source nucleotides. "Essentially pure" nucleotide means a composition comprising at least about 90% by weight of the nucleotide, based on total weight of the composition, typically at least about 95% by weight, more typically at least about 90% by weight, even more typically at least about 95% by weight, and even more typically at least about 99% by weight of nucleotide, based on total weight of the composition.

As used herein, "treatment" or "therapy" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of cellular degeneration or damage, such as the pathology of immune cells in inflammatory reactions or the pathology of organ cells in sepsis, or may render the cells more susceptible to treatment or therapy by other therapeutic agents.

The terms "therapeutically effective amount", "effective amount" or "sufficient amount" mean a quantity sufficient, when administered to a subject, including a mammal, for example a human, to achieve a desired result, for example an amount effective to treat sepsis. Effective amounts of the agents described herein may vary according to factors such as the disease state, age, sex, and weight of the subject. Dosage or treatment regimes may be adjusted to provide the optimum therapeutic response, as is understood by a skilled person.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The agents of the present invention may, in aspects, be administered before, during or after treatment with conventional therapies for the disease or disorder in question, such as sepsis.

The term "subject" as used herein refers to any member of the animal kingdom, typically a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers that are non-toxic to the cell or mammal being exposed thereto at the dosages and concentrations employed. Often the pharmaceutically acceptable carrier is an aqueous pH buffered solution. Examples of pharmacologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, and dextrins; chelating agents such as EDTA; sugar alcohols such as mannitol and sorbitol; salt-forming counterions such as sodium; and/or nonionic surfactants such as TWEEN™, polyethylene glycol (PEG), and PLURONICS™.

A "liposome" is a small vesicle composed of various types of lipids, phospholipids and/or surfactant which is useful for delivery of a drug to a subject, such as a mammal. The components of the liposome are commonly arranged in a bilayer formation, similar to the lipid arrangement of biological membranes.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component or sequence defined herein as being included may be explicitly excluded from the claimed invention by way of proviso or negative limitation. Similarly, the subject or patient to be treated may be defined as having or not having any of the symptoms or outcomes of sepsis described herein or known to a skilled person.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Inflammation

Inflammatory disorders are usually mediated by an inflammatory cytokine cascade, defined herein as an in vivo release from cells of at least one proinflammatory cytokine in a subject, wherein the cytokine release affects a physiological condition of the subject. Non-limiting examples of cells that produce proinflammatory cytokines are monocytes, macrophages, neutrophils, epithelial cells, osteoblasts, fibroblasts, smooth muscle cells, and neurons.

A "cytokine" is a soluble protein or peptide which is naturally produced by mammalian cells and which act in vivo as humoral regulators at micro- to picomolar concentrations. Cytokines can, either under normal or pathological conditions, modulate the functional activities of individual cells and tissues. A proinflammatory cytokine is a cytokine that is capable of causing any of the following physiological reactions associated with inflammation: vasodialation, hyperemia, increased permeability of vessels with associated edema, accumulation of granulocytes and mononuclear phagocytes, or deposition of fibrin. Non-limiting examples of proinflammatory cytokines are tumor necrosis factor alpha (TNF), interleukin (IL)-Ia, IL-I-beta, IL-6, IL-8, IL-18, interferon-gamma, HMG-1, platelet-activating factor (PAF), and macrophage migration inhibitory factor (MIF). Proinflammatory cytokines can mediate deleterious conditions for many inflammatory disorders, for example endotoxic shock, asthma, rheumatoid arthritis, inflammatory bile disease, heart failure, and allograft rejection.

Proinflammatory cytokines are to be distinguished from anti-inflammatory cytokines, such as IL-4, IL-10, and IL-13, which are not mediators of inflammation. In certain examples, release of anti-inflammatory cytokines is not inhibited by the treatment described herein.

In certain examples, the treatment described herein inhibits the proinflammatory effect of TNF. TNF serves as a mediator in various inflammatory disorders. A few such examples include: septic shock, cancer, AIDS, transplantation rejection, multiple sclerosis, diabetes, rheumatoid arthritis, trauma, malaria, meningitis, ischemia-reperfusion injury, and adult respiratory distress syndrome.

TNF plays a role in several inflammatory disorders, and thus research has been conducted concerning TNF therapies and anti-TNF therapies. Research has focused upon inhibition of TNF activity in such inflammatory disorders as rheumatoid arthritis, Crohn's disease, AIDS, bacterial septic shock (caused by certain gram negative bacteria), and bacterial toxic shock (caused by superantigens) as well as in prevention of alloreactivity and graft rejection. Mutant mice that lack TNF are resistant to gram-negative bacteria induced sepsis (Janeway, C., Travers, P., Walport, M., Capra, J. Immunobiology: The Immune System in Health and Disease. New York, N.Y.: Garland Publishers. 1999), and anti-TNF monoclonal antibodies have been used to inhibit TNF activity and treat endotoximia (Beutler, et al., Science 229; 867-871). One advantage of treatment to control TNF activity results from its role in multiple types of inflammation. For example, it is often difficult to determine that inflammation in burn and trauma victims are of infectious etiology and warrant treatment with antibiotics; therefore treatment to inhibit TNF activity may be beneficial. Strategies for inhibition of TNF activity include neutralization of the cytokine via either anti-TNF antibodies, soluble receptors, or receptor fusion proteins; suppression of TNF-A synthesis via drugs such as cyclosporine A, glucocorticoides, or cytokine IL-10; reduction of responsiveness to TNF via repeated low dose stimulation; or by inhibition of secondary mediators such as IL-1, IL-6, or nitric oxide. The agents described herein can be used to inhibit TNF activity.

An inflammatory disorder can be one where an inflammatory cytokine cascade causes a systemic reaction, such as with systemic inflammatory response syndrome (SIRS) or septic shock. Alternatively, the disorder can be mediated by a localized inflammatory cytokine cascade, as in rheumatoid arthritis. Non-limiting examples of conditions which can be usefully treated using the agents described herein include appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitits, hepatitis, Crohn's disease, enteritis, Whipple's disease, allergy, anaphylactic shock, immune complex disease, multiple organ dysfunction syndrome (MODS), organ ischemia, reperfusion injury, organ necrosis, hay fever, systemic inflammatory response syndrome (SIRS), sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitits, alvealitis, bronchiolitis, pharyngitis, pleurisy, sinusitis, influenza, respiratory syncytial virus infection, HIV infection, AIDS, hepatitis B virus infection, hepatitis C virus infection, herpes virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, obesity, ankylosing spondylitis, Berger's disease, Reiter's syndrome and Hodgkin's disease.

In certain non-limiting examples, the inflammatory disorder is selected from asthma, allergy, anaphylactic shock, multiple organ dysfunction syndrome (MODS), organ ischemia, ischaemia-reperfusion injury, organ necrosis, SIRS, sepsis, septicemia, endotoxic shock, cachexia, septic abortion, disseminated bacteremia, burns, coeliac disease, congestive heart failure, myocarditis, myocardial ischemia adult respiratory distress syndrome, cerebral infarction, cerebral embolism, spinal cord injury, paralysis, allograft rejection or graft-versus-host disease.

In one example, the inflammatory disorder is endotoxic shock. In another example, the inflammatory disorder is SIRS. In still another example, the inflammatory disorder is sepsis. In yet another example, the inflammatory disorder is multiple organ dysfunction syndrome (MODS).

Sepsis

Sepsis is a systemic inflammatory response to infection and the most common cause of death in intensive care units. Mortality is 20-30% in sepsis and 40-80% in septic shock (Angus et al., Crit Care Med 2001; 29:1303-1310). Myocardial dysfunction is a common complication of septic shock (Parrillo et al., Ann Intern Med 1990; 113:227-242). This systemic inflammatory disorder is a result of a dysregulated host response to infection and is characterized by excessive pro-inflammatory cytokine production. Initiation of the host's innate immune response is mediated through the activation of the cell membrane toll-like receptor-4 (TLR4) in recognizing pathogen-associated molecular patterns (PAMPs). Lipopolysaccharide (LPS) is the most prominent PAMP in the outer membrane of Gram-negative bacteria and binds to TLR4 in a CD-14 and LPS binding protein (LBP) dependent manner. Activation of TLR4 upon LPS binding initiates a signalling pathway that leads to the activation of the mitogen-activated protein kinases (MAPK) and production of TNF, a prominent cytokine which is a major contributing factor in organ dysfunction (for example, cardiac dysfunction) in sepsis (Suffredini et al., N Engl J Med 1989; 321:280-287; Natanson et al., J Exp Med 1989; 169:823-832).

Sepsis is considered present if infection is highly suspected or proven and two or more of the following systemic inflammatory response syndrome (SIRS) criteria are met (Bone R C, Balk R A, Cerra F B, et al (June 1992). "Definitions for sepsis and organ failure and guidelines for the use of innovative therapies in sepsis. The ACCP/SCCM Consensus Conference Committee. American College of Chest Physicians/Society of Critical Care Medicine". Chest 101 (6): 1644-55.):

Heart rate >90 beats per minute (tachycardia);
Body temperature <36° C. (96.8° F.) or >38° C. (100.4° F.) (hypothermia or fever);
Respiratory rate >20 breaths per minute or, on blood gas, a PaCO2 less than 32 mm Hg (4.3 kPa) (tachypnea or hypocapnia due to hyperventilation);
White blood cell count <4000 cells/mm$^3$ or >12000 cells/mm$^3$ (<4×10$^9$ or >12×10$^9$ cells/L), or greater than 10% band forms (immature white blood cells); (leukopenia, leukocytosis, or bandemia).

Fever and leukocytosis are features of the acute phase reaction, while tachycardia is often the initial sign of hemodynamic compromise. Tachypnea may be related to the increased metabolic stress due to infection and inflammation, but may also be a sign of inadequate perfusion resulting in the onset of anaerobic cellular metabolism.

In children, the SIRS criteria are modified in the following fashion (Goldstein B, Giroir B, Randolph A (2005). "International pediatric sepsis consensus conference: definitions for sepsis and organ dysfunction in pediatrics". Pediatr Crit Care Med 6 (1): 2-8):

Heart rate >2 standard deviations above normal for age in the absence of stimuli such as pain and drug administration, OR unexplained persistent elevation for greater than 30 minutes to 4 hours. In infants, also includes Heart rate <10th percentile for age in the absence of vagal stimuli, beta-blockers, or congenital heart disease OR unexplained persistent depression for greater than 30 minutes;
Body temperature obtained orally, rectally, from Foley catheter probe, or from central venous catheter probe >38.5° C. or <36° C. Temperature must be abnormal to qualify as SIRS in pediatric patients;
Respiratory rate >2 standard deviations above normal for age OR the requirement for mechanical ventilation not related to neuromuscular disease or the administration of anesthesia;
White blood cell count elevated or depressed for age not related to chemotherapy, or greater than 10% bands+ other immature forms.

As will be recognized by the skilled person SIRS criteria must be interpreted carefully within the clinical context. These criteria exist primarily for the purpose of more objectively classifying critically-ill patients so that future clinical studies may be more rigorous and more easily reproducible.

Consensus definitions continue to evolve with the latest list of signs and symptoms of sepsis to reflect clinical bedside experience.

To qualify as sepsis, there must be an infection suspected or proven (by culture, stain, or polymerase chain reaction (PCR)), or a clinical syndrome pathognomonic for infection. Specific evidence for infection includes WBCs in normally sterile fluid (such as urine or cerebrospinal fluid (CSF), evidence of a perforated viscus (free air on abdominal x-ray or CT scan, signs of acute peritonitis), abnormal chest x-ray (CXR) consistent with pneumonia (with focal opacification), or petechiae, purpura, or purpura fulminans The more critical subsets of sepsis are severe sepsis (sepsis with acute organ dysfunction) and septic shock (sepsis with refractory arterial hypotension). Alternatively, when two or more of the systemic inflammatory response syndrome criteria are met without evidence of infection, patients may be diagnosed simply with "SIRS." Patients with SIRS and acute organ dysfunction may be termed "severe SIRS."

Patients are defined as having "severe sepsis" if they have sepsis plus signs of systemic hypoperfusion: either organ dysfunction or a serum lactate greater than 4 mmol/dL. Other signs include oliguria and altered mental status. Patients have also been defined as having septic shock if they have sepsis plus hypotension after aggressive fluid resuscitation (typically upwards of 6 liters or 40 ml/kg of crystalloid).

Examples of end-organ dysfunction include the following (Abraham E, Singer M (2007). "Mechanisms of sepsis-induced organ dysfunction". Crit. Care Med. 35 (10): 2408-16):

Lungs—acute lung injury (ALI) ($PaO_2/FiO_2<300$) or acute respiratory distress syndrome (ARDS) ($PaO_2/FiO_2<200$);
Brain—encephalopathy—(symptoms: agitation, confusion, coma); (etiologies: ischemia, hemorrhage, microthrombi, microabscesses, multifocal necrotizing leukoencephalopathy);
Liver—disruption of protein synthetic function: manifests acutely as progressive coagulopathy due to inability to synthesize clotting factors; disruption of metabolic functions: manifests as cessation of bilirubin metabolism, resulting in elevated unconjugated serum bilirubin levels (indirect bilirubin);
Kidney—oliguria and anuria; electrolyte abnormalities; volume overload;
Heart—systolic and diastolic heart failure, at least in part due to cytokines that depress myocyte function; cellular damage, manifest as a troponin leak (although not necessarily ischemic in nature).

MicroRNAs

The present invention encompasses agents that interact with miRNA sequences and therefore modulate the function and/or activity of the miRNA. Typically the miRNA sequences that are targeted by the agents described herein include any miRNAs that target and inhibit anti-apoptotic protein expression, including members of the miRNA-15 family, such as mir-15a, mir-15b, miR-16, miR-195, mir-322/424, and miR-497. The sequences for these members of the miR-15 family are as follows:

miR-15a:
5' uagcagcacauaaugguuugug 3' miR-15b:
5' uagcagcacaucaugguuuaca 3' miR-16:
5' uagcagcacguaaauauuggcg 3' miR-195:
5' uagcagcacagaaauauuggc 3' miR-322/424:
5' cagcagcaauucauguuuugga 3' miR-497:
5' cagcagcacacugugguuugua 3'

These miRNAs have been shown to be upregulated in conditions such as sepsis and would thus be responsible for inhibiting expression of specific genes involved in sepsis. By inhibiting one or more of these miRNAs, their inhibition of the genes involved in sepsis is blocked and expression of these genes is permitted, thus treating the sepsis.

MicroRNA Inhibitory Agents

The agents described herein interact with specific miRNA sequences and thereby modulate their function and/or activity. Combinations of agents may also be employed and may act together synergistically or additively. The agents may specifically bind to miRNA sequences and silence them via antisense or siRNA technology or they may be corresponding miRNA target sequences or variants or fragments thereof that compete with native miRNA target sequences for inhibition by the miRNA in question.

Typically, the agent is an antagomir, which is a chemically engineered oligonucleotide that prevents other molecules, such as miRNAs from binding to a desired site on an mRNA molecule. The term "antagomir" refers to a single-stranded, double-stranded, partially double-stranded or hairpin-structured oligomer or polymer of ribonucleic acid (RNA) or deoxyribonucleic acid (DNA) or both or modifications thereof, which is antisense with respect to its miRNA target.

Examples of antagomirs and other miRNA inhibitors are described in WO2009/20771, WO2008/91703, WO2008/046911, WO2008/074328, WO2007/90073, WO2007/27775, WO2007/27894, WO2007/21896, WO2006/93526, WO2006/112872, WO2007/112753, WO2007/1 12754, WO2005/23986, or WO2005/13901, all of which are hereby incorporated by reference.

Custom designed antagomir molecules are commercially available from, for example, Applied Biosystems. These molecules are chemically modified and optimized single-stranded nucleic acids designed to specifically inhibit naturally occurring mature miRNA molecules in cells. For example, product ID AM12607 from Applied Biosystems is an Ambion® Anti-miR™ inhibitor targeting human miR-33a.

Antagomirs are also commercially available from Thermo Scientific. These inhibitors include chemical modifications and secondary structure motifs. For example, Vermeulen et al. reports in U.S. Patent Publication 2006/0223777 the identification of secondary structural elements that enhance the potency of these molecules. Specifically, incorporation of highly structured, double-stranded flanking regions around the reverse complement core significantly increases inhibitor function and allows for multi-miRNA inhibition at subnanomolar concentrations. Other such improvements in antagomir design are contemplated for use in the disclosed methods.

In aspects, the antagomir includes a region of sufficient nucleotide length and sufficient complementarity to the miRNA of interest that the antagomir forms a duplex with the miRNA. Given the sequence of the miRNA in question, an antagomir can be designed according to the rules of Watson and Crick base pairing.

Thus, the antagomir can be an antisense oligonucleotide having a single-stranded nucleic acid sequence that is complementary to at least 8, 9, 10, 11, 12, 13, 14, 15, 16, 17, 18, 19, 20, 21, 22, 23, or 24 contiguous nucleotides in the miRNA in question, wherein the antisense oligonucleotide forms a duplex with the miRNA under physiological conditions.

The antagomir can include an antisense oligonucleotide having a length of at least 8 contiguous nucleotides. Therefore, the antisense oligonucleotide can have 8, 9, 10, 11, 12, 13, 14, 15, 16, 17, 18, 19, 20, 21, 22, 23, or 24 contiguous nucleotides. The oligonucleotide is typically less than 30 contiguous nucleotides in length. The oligonucleotide can be less than 25, 26, 27, 28, 29, 30, 31, 32, 33, 34, 35, 36, 37, 38, 39, 40 contiguous nucleotides in length The disclosed antagomir can include an antisense oligonucleotide having a region that is at least partially, and in some aspects fully, complementary to the miRNA of interest. It is not necessary that there be perfect complementarity between the antagomir and the target, but the correspondence must be sufficient to enable the antisense oligonucleotide to duplex with miRNA and subsequently reduce its activity. For example, in typical aspects, the antisense oligonucleotide inhibits binding of the miRNA to its mRNA target.

The disclosed antagomir can include an antisense oligonucleotide having a region that is at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% complementary to the miRNA of interest.

Typically, the disclosed antagomir has at least 6, 7, 8, 9, 10, 11, 12, 13, 14, 15, 16, 17, 18, 19, 20 or more contiguous nucleotides complementary to the nucleotide sequence of the miRNA of interest. In one aspect, the disclosed antagomir has a nucleotide sequence that is complementary to the miRNA of interest. Thus, in one aspect, the disclosed antagomir has at least 6, 7, 8, 9, 10, 11, 12, 13, 14, 15, 16, 17, 18, 19, 20 or more contiguous nucleotides that are complementary to the miRNA of interest.

In some aspects, there will be nucleotide mismatches in the region of complementarity. In a typical aspect, the region of complementarity will have no more than 1, 2, 3, 4, or 5 mismatches.

In some aspects, the antagomir is "exactly complementary" to the miRNA of interest. Thus, in one aspect, the antagomir can anneal to the miRNA of interest to form a hybrid made exclusively of Watson-Crick base pairs in the region of exact complementarity. Thus, in some aspects, the antagomir specifically discriminates a single-nucleotide difference. In this case, the antagomir only inhibits miRNA activity if exact complementarity is found in the region of the single-nucleotide difference.

The disclosed antagomirs include oligomers or polymers of ribonucleic acid (RA) or deoxyribonucleic acid (DNA) or both or modifications thereof. This term includes oligonucleotides composed of naturally occurring nucleobases, sugars, and covalent internucleoside (backbone) linkages as well as oligonucleotides having non-naturally-occurring portions that function similarly. Such modified or substituted oligonucleotides are often used over native forms because of desirable properties such as, for example, enhanced cellular uptake, enhanced affinity for nucleic acid target, and/or increased stability in the presence of nucleases.

The antagomir oligonucleotide can include unmodified RNA and DNA as well as RNA and DNA that have been modified, e.g., to improve efficacy, and polymers of nucleoside surrogates. "Unmodified" RNA refers to a molecule in which the components of the nucleic acid, namely sugars, bases, and phosphate moieties, are the same or essentially the same as that which occur in nature, typically as occur naturally in the human body. "Modified" RNA, as used herein, refers to a molecule where one or more of the components of the nucleic acid, namely sugars, bases, and phosphate moieties, are different from that which occur in nature, typically different from that which occurs in the human body. While they are referred to as "modified RNAs" they will of course, because of the modification, include molecules that are not, strictly speaking, RNAs.

The disclosed antagomir oligonucleotide can be modified to enhance resistance to nucleases. The antagomir oligonucleotide can include nucleotide modification that stabilized it against nucleolytic degradation. The oligomer can be a totalmer, mixmer, gapmer, tailmer, headmer or blockmer. A "totalmer" is a single stranded oligonucleotide that only comprises non-naturally occurring nucleotides.

The term "gapmer" refers to an oligonucleotide composed of modified nucleic acid segments flanking at least 5 naturally occurring nucleotides (i.e., unmodified nucleic acids).

The term "blockmer" refers to a central modified nucleic acid segment flanked by nucleic acid segments of at least 5 naturally occurring nucleotides.

The term "tailmer" refers to an oligonucleotide having at least 5 naturally occurring nucleotides at the 5'-end followed by a modified nucleic acid segment at the 3'-end.

The term "headmer" refers to oligonucleotide having a modified nucleic acid segment at the 5'-end followed by at least 5 naturally occurring nucleotides at the 3'-end. The term "mixmer" refers to oligonucleotides that comprise both naturally and non-naturally occurring nucleotides. However, unlike gapmers, tailmers, headmers and blockmers, there is no contiguous sequence of more than 5 naturally occurring nucleotides, such as DNA units.

Modified nucleic acids and nucleotide surrogates can include one or more of: (i) replacement of one or both of the non-linking phosphate oxygens and/or of one or more of the linking phosphate oxygens; (ii) replacement of a constituent of the ribose sugar, e.g., of the 2' hydroxyl on the ribose sugar, or wholesale replacement of the ribose sugar with a structure other than ribose; (iii) wholesale replacement of the phosphate moiety with "dephospho" linkers; (iv) modification or replacement of a naturally occurring base; (v) replacement or modification of the ribose-phosphate backbone; or (vi) modification of the 3' end or 5' end of the RNA, e.g., removal, modification or replacement of a terminal phosphate group or conjugation of a moiety, such as a fluorescently labeled moiety, to either the 3' or 5' end of RNA.

The phosphate group in a nucleic acid can be modified by replacing one of the oxygen atoms with a different substituent. One result of this modification to RNA phosphate backbones can be increased resistance of the oligoribonucleotide to nucleolytic breakdown. Thus, it can be desirable in some aspects to introduce alterations that result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur.

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen.

The phosphate group can be replaced by non-phosphorus containing connectors. Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Typical replacements include the methylenecarbonylamino and methylenemethylimino groups.

A modified RNA can include modification of all or some of the sugar groups of the ribonucleic acid. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the hydroxyl is connected, e.g., by a methylene bridge, to the 4' carbon of the same ribose sugar; amine, 0-AMINE and aminoalkoxy, $O(CH_2)_n$ AMINE, (e.g., AMINE=N¾; alkylamino, dialkylamino, heterocyclyl amino, arylamino, diaryl amino, heteroaryl amino, or diheteroaryl amino, ethylene diamine, polyamino). Oligonucleotides containing only the methoxyethyl group (MOE) ($OCH_2CH_2OCH_3$, a PEG derivative) exhibit nuclease stabilities comparable to those modified with the robust phosphorothioate modification.

"Deoxy" modifications include hydrogen (i.e., deoxyribose sugars); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH$ AMINE (AMINE=$NH_2$; alkylamino, dialkylamino, heterocyclyl amino, arylaamino, diaryl amino, heteroaryl amino, or diheteroaryl amino), —NHC(O)R (R^alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Thus, the antagomir can include a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In some aspects, the antagomir includes at least one 2'-O-methyl-modified nucleotide, and in some aspects, all of the nucleotides of the antagomir include a 2'-O-methyl modification.

The sugar group can also contain one or more carbons that possess the opposite stereochemical configuration than that of the corresponding carbon in ribose. Thus, a modified RA can include nucleotides containing e.g., arabinose, as the sugar.

Modified RNAs can also include "abasic" sugars, which lack a nucleobase at C—P. These abasic sugars can also further contain modifications at one or more of the constituent sugar atoms. The modification can also entail the wholesale replacement of a ribose structure with another entity (an SRMS) at one or more sites in the oligonucleotide agent.

The 3' and 5' ends of an oligonucleotide can be modified. Such modifications can be at the 3' end, 5' end, or both ends of the molecule. They can include modification or replacement of an entire terminal phosphate or of one or more of the atoms of the phosphate group. For example, the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based, e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —(CH$_2$)$_n$—, —(CH$_2$)$_n$N—, —(CH—$_2$)$_n$O—, —(CH$_2$)$_n$S—, O(C¾CH$_2$O)$_n$¾O¾OH (e.g., N™3 or 6), abasic sugars, amide, carboxy, amine, oxyamine, oxyimine, thioether, disulfide, thiourea, sulfonamide, or morpholino, or biotin and fluorescein reagents.

Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, 03-(oleoyl)lithocholic acid, 03-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40), MPEG, [MPEG]2, polyaraino, alkyl, substituted aikyl, radiolabeled markers, enzymes, haptens (e.g. biotin), transport absorption facilitators (e.g., aspirin, vitamin E, folic acid), synthetic ribonucleases (e.g., imidazole, bisimidazole, histamine, imidazole clusters, acridine-imidazole conjugates, Eu$^{3+}$ complexes of tetraazamacrocycles), Terminal modifications include the addition of a methylphosphonate at the 3'-most terminal linkage; a 3' C5-ammoalkyl-dT; 3' cationic group; or another 3' conjugate to inhibit 3'-5' exonucleolytic degradation.

Terminal modifications useful for modulating activity include modification of the 5' end with phosphate or phosphate analogs. For example, in some aspects, oligonucleotide agents are 5' phosphorylated or include a phosphoryl analog at the 5' terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P"O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5f-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P—NH-5\(HO)(NH$_2$)(O)P—O-5'), 5'-alkylphosphonates (R=alkyl-methyl, ethyl, isopropyl, propyl, etc., e.g. RP(OH)(O)—O-5\(OH)$_2$(O)P-5'-CH$_2$—), 5'-alkyletherphosphonates (R=alkylether=methoxymethyl (MeOCH$_2$—), ethoxymethyl, etc., e.g. RP(OH)(O)—O-5'-).

Adenine, guanine, cytosine and uracil are the most common bases found in RNA. These bases can be modified or replaced to provide RNAs having improved properties. For example, nuclease resistant oligonucleotides (i.e., oligoribonucleotides) can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases" and "universal bases", can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosinej-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil5 5-methylaminomethyl-2-thiouracil, 3-(3-amino-3carboxypropyl)uracil, 3-methylcytosine, 5-methylcytosine, N$^4$-acetyl cytosine, 2-thiocytosine, N6-methyladenine, N6-isopentyladenine, 2-methylthio-N6-isopentenyladenine, N-methylguanines, or O-alkylated bases. The antagomir can include an internucleotide linkage (e.g., the chiral phosphorothioate linkage) useful for increasing nuclease resistance.

Phosphorothioates (or S-oligos) are a variant of normal DNA or RNA in which one of the nonbridging oxygens is replaced by a sulfur. The sulfurization of the internucleotide bond dramatically reduces the action of endo- and exonucleases including 5' to 3' and 3' to 5' DNA POL 1 exonuclease, nucleases SI and PI, RNases, plasma nucleases and snake venom phosphodiesterase. In addition, the potential for crossing the lipid bilayer increases. Because of these important improvements, phosphorothioates have found increasing application in cell regulation.

Phosphorothioates are made by two principal routes: by the action of a solution of elemental sulfur in carbon disulfide on a hydrogen phosphonate, or by the more recent method of sulfurizing phosphite triesters with either tetraethylthiuram disulfide (TETD) or 3H-1,2-bensodithiol-3-one-1,1-dioxide (BDTD).

One way to increase resistance is to identify cleavage sites and modify such sites to inhibit cleavage. For example, the dinucleotides 5'-UA-3', 5'-UG-3\ 5'-CA-3\ 5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2*-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a—modified nucleotide; or at least one 5'-cytidine-cytidine-3' (5'-CC-3') dinucleotide, wherein the 5'-cytidine is a 2'-modified nucleotide. Thus, the antagomir can include at least 2, 3, 4 or 5 of such dinucleotides. In certain aspects, all the pyrimidines of an antagomir carry a 2'-modification, and the antagomir therefore has enhanced resistance to endonucleases.

An antagomir can have secondary structure, but it is typically substantially single-stranded under physiological conditions at least in the region of the antagomir that is complementary to the miRNA. An antagomir that is substantially single-stranded is single-stranded to the extent that less than about 50% (e.g., less than about 40%, 30%, 20%, 10%, or 5%) of the antagomir is duplexed with itself. Thus, the antagomir typically does not form hairpin loops, bulges or internal loops within the complementary region under physiological conditions.

In a typical aspect, the antagomir does not include a sense strand. In some aspects, the antagomir is partially double-stranded but is single-stranded at least in the region of the antagomir that is complementary to the miRNA. The term "partially double-stranded" refers to double stranded structures wherein one strand contains fewer nucleotides than its complementary strand. In general, such partial double stranded agents will have less than 75% double stranded structure, typically less than 50%, and more typically less than 25%, 20% or 15% double stranded structure.

In a typical aspect, the antagomir is suitable for delivery to a cell in vivo, e.g., to a cell in an organism. In another aspect, the antagomir is suitable for delivery to a cell in vitro, e.g., to a cell in a cell line in culture or a suspension. The antagomir can include a ligand that is selected to improve stability, distribution or cellular uptake of the agent. For example, the ligand can be a lipophilic moiety, e.g., cholesterol, which enhances entry of the antagomir into a cell.

The antagomir can also be encapsulated by cationic lipid particles. Cationic lipid saturation influences intracellular delivery of encapsulated nucleic acids. Cationic lipids include 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA) and 1,2-dilinolenyloxy-N,N-dimethyl-3-aminopropane (DLenDMA).

In some aspects, the disclosed antagomir can include an aminoglycoside ligand, which can cause the antagomir to have improved hybridization properties or improved sequence specificity. Exemplary aminoglycosides include glycosylated polylysine; galactosylated polylysine; neomycin B; tobramycin; kanamycin A; and acridine conjugates of aminoglycosides, such as Neo-N-acridine, Neo-S-acridine, Neo-C-acridine, Tobra-N-acridine, and KanaA~N-acridine. Use of an acridine analog can increase sequence specificity. For example, neomycin B has a high affinity for RNA as compared to DNA, but low sequence-specificity. In some aspects the guanidine analog (the guanidinoglycoside) of an aminoglycoside ligand is tethered to an oligonucleotide agent. In a guanidinoglycoside, the amine group on the amino acid is exchanged for a guanidine group. Attachment of a guanidine analog can enhance cell permeability of an oligonucleotide agent.

The disclosed antagomir can be expressed within cells from an expression vector having a nucleic acid encoding the antagomir. The nucleic acid sequence can be operably linked to an expression control sequence, such as a promoter. Those skilled in the art realize that any nucleic acid can be expressed in eukaryotic cells from the appropriate DNA RNA vector.

Thus, the disclosed antagomir can be expressed from transcription units inserted into DNA or RNA vectors. The recombinant vectors can be DNA plasmids or viral vectors. Oligonucleotide agent-expressing viral vectors can be constructed based on, but not limited to, adeno-associated virus, retrovirus, lentivirus, adenovirus, or alphavirus. The recombinant vectors capable of expressing the oligonucleotide agents can be delivered as described above, and can persist in target cells. Alternatively, viral vectors can be used that provide for transient expression of nucleic acid molecules. Such vectors can be repeatedly administered as necessary. Once expressed, the disclosed antagomir interacts with the miRNA of interest and inhibits its activity. In typical aspects, the at least part of the antagomir forms a duplex with an endogenous miRNA, which prevents the endogenous miRNA from binding to its target mRNA, which results in increased translation of the target mRNA. Delivery of oligonucleotide agent-expressing vectors can be systemic, such as by intravenous or intramuscular administration, by administration to target cells ex-planted from a subject followed by reintroduction into the subject, or by any other means that would allow for introduction into the desired target cell (for a review see Couture et al., Trends in Genetics 12:510, 1996).

The agent can also be a small molecule inhibitor. As used herein, the term "small molecule" refers to small organic compounds, inorganic compounds, or any combination thereof that inhibits or reduces the activity of the miRNA in question; this term may include monomers or primary metabolites, secondary metabolites, a biological amine, a steroid, or synthetic or natural, non-peptide biological molecule(s).

For example, Huang and his colleagues developed a method to identify inhibitors of miRNA pathways in live human cells (Angew Chem Int Ed Engl. 2008; 47(39):7482-4). Specifically, they designed a screening assay to look for small molecules or compounds that selectively repress miRNA. They selected miR-21 as the target agent due to its documented role in preventing cell death—thereby allowing the unchecked cell proliferation associated with cancer— and its elevated levels in various cancers. Their assay contained the DNA binding sequence complementary to the miRNA, bound to a reporter such as luciferase. Under normal conditions, the miRNA binds to the complementary sequence and inhibits the translation of the reporter, such as luciferase. Candidate agents were then be added to the sample to determine whether the candidate agent reduced miRNA inhibition of reporter expression.

Thus, a method is provided that involves providing a sample having an oligonucleotide with a DNA binding sequence complementary to the miRNA of interest under conditions that allow the binding of the miRNA of interest to the oligonucleotide, contacting the sample with a candidate agent, detecting the level of miRNA/oligonucleotide binding, comparing the binding level to a control, a decrease in miRNA/oligonucleotide binding compared to the control identifying an miRNA inhibitor.

The binding of miRNA to the oligonucleotide can be detected using routine methods. In a typical aspect, the DNA binding sequence complementary to the miRNA of interest is operably linked to a reporter construct, such as luciferase or GFP, wherein binding of the miRNA of interest to the oligonucleotide inhibits reporter expression. In general, candidate agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

When a crude extract is found to have a desired activity, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits miRNA. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases or conditions, such as those disclosed herein.

Candidate agents encompass numerous chemical classes, but are most often organic molecules, e.g., small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, for example, at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In a further aspect, candidate agents are peptides.

In some aspects, the candidate agents are proteins. In some aspects, the candidate agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the methods herein. The libraries can be bacterial, fungal, viral, and vertebrate proteins, and human proteins.

An antagomir, such as a single-stranded oligonucleotide agent, can be constructed using chemical synthesis and/or enzymatic ligation reactions using procedures known in the art. For example, an antagomir can be chemically synthesized using naturally occurring nucleotides or variously modified nucleotides designed to increase the biological stability of the molecules or to increase the physical stability of the duplex formed between the antagomir and target nucleic acids, e.g., phosphorothioate derivatives and acridine substituted nucleotides can be used. Other appropriate nucleic acid modifications are described herein. Alternatively, the antagomir can be produced biologically using an expression vector into which a nucleic acid has been subcloned in an antisense orientation (i.e., RNA transcribed from the inserted nucleic acid will be of an antisense orientation to a target miRNA of interest.

The agents described herein may be formulated into compositions, which may further comprise one or more pharmaceutically acceptable excipients, carriers, buffers, stabilizers, adjuvants, or mixtures thereof.

Therapeutic compositions of the agents are prepared for storage by mixing the desired agent having the appropriate degree of purity with optional pharmaceutically acceptable carriers, excipients, and/or stabilizers (Remington's Pharmaceutical Sciences, 16th edition, Osol, A. ed. (1980), incorporated herein by reference in its entirety), in the form of lyophilized formulations or aqueous solutions. Acceptable carriers, excipients, or stabilizers are nontoxic to recipients at the dosages and concentrations employed and are described above.

Additional examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of the agents include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms may be used. Such forms include, for example, microcapsules, nano-capsules, liposomes, plasters, inhalation forms, nose sprays, sublingual tablets, and sustained-release preparations.

The agents will typically be formulated in such vehicles at a concentration of about 0.01 mg/ml to about 100 mg/ml, such as about 0.1 to about 1 mg/ml, or typically about 0.4 mg/ml for plasmid DNA and such as about 1 to about 10 mg/ml or typically about 4 mg/ml for antisense oligos.

Agents to be used for in vivo administration are generally sterile. This is readily accomplished, for example, by filtration through sterile filtration membranes, prior to or following lyophilization and reconstitution. The agents ordinarily will be stored in lyophilized form or in solution if administered systemically. If in lyophilized form, the agents are typically formulated in combination with other ingredients for reconstitution with an appropriate diluent at the time of use. An example of a liquid formulation of the agents described herein is a sterile, clear, colorless unpreserved solution filled in a single-dose vial for subcutaneous injection. Preserved pharmaceutical compositions suitable for repeated use may contain, for example, depending mainly on the indication and type of agent: the agent; a buffer capable of maintaining the pH in a range of maximum stability of the agent in solution, typically about 4-8; a detergent/surfactant primarily to stabilize the agent against agitation-induced aggregation; an isotonifier; a preservative selected from the group of phenol, benzyl alcohol and a benzethonium halide, e.g., chloride; and water.

If the detergent employed is non-ionic, it may, for example, comprise polysorbates (e.g., POLYSORBATE™ (TWEEN™) 20, 80, etc.) or poloxamers (e.g., POLOXAMER™ 188). The use of non-ionic surfactants permits the formulation to be exposed to shear surface stresses without causing denaturation of the agent. Further, such surfactant-containing formulations may be employed in aerosol devices such as those used in a pulmonary dosing, and needleless jet injector guns (see, e.g., EP 257,956, incorporated herein by reference in its entirety).

An isotonifier may be present to ensure isotonicity of a liquid composition of the agents described herein, and includes polyhydric sugar alcohols, typically trihydric or higher sugar alcohols, such as glycerin, erythritol, arabitol, xylitol, sorbitol, and mannitol. These sugar alcohols can be used alone or in combination. Alternatively, sodium chloride or other appropriate inorganic salts may be used to render the solutions isotonic.

The buffer may, for example, be an acetate, citrate, succinate, or phosphate buffer depending on the pH desired. The pH of one type of liquid formulation of this invention is buffered in the range of about 4 to 8, typically about physiological pH.

The preservatives phenol, benzyl alcohol and benzethonium halides, e.g., chloride, are known antimicrobial agents that may be employed.

Therapeutic compositions described herein generally are placed into a container having a sterile access port, for example, an intravenous solution bag or vial having a stopper pierceable by a hypodermic injection needle. The formulations are typically administered as repeated intravenous (i.v.), subcutaneous (s.c.), or intramuscular (i.m.) injections, or as aerosol formulations suitable for intranasal or intrapulmonary delivery (for intrapulmonary delivery see, e.g., EP 257,956, incorporated herein by reference in its entirety).

An article of manufacture, such as a kit containing an agent useful for the treatment of the disorders described herein, comprises at least a container and a label. Suitable containers include, for example, bottles, vials, syringes, and test tubes. The containers may be formed from a variety of materials such as glass or plastic. The container holds a composition that is effective for diagnosing or treating the condition and may have a sterile access port (for example, the container may be an intravenous solution bag or a vial having a stopper pierceable by a hypodermic injection needle). The active agent in the composition is an agent described herein. The label on, or associated with, the container indicates that the composition is used for treating the condition of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use. The article of manufacture may also comprise a second or third container with another active pharmaceutical agent as described herein.

The agents described herein can also be administered in the form of sustained-released preparations. Suitable examples of sustained-release preparations include semipermeable matrices of solid hydrophobic polymers containing the agent, which matrices are in the form of shaped articles, e.g., films or microcapsules. Examples of sustained-release matrices include polyesters, hydrogels (e.g., poly(2-hydroxyethyl-methacrylate) as described by Langer et al., J. Biomed. Mater. Res. 15:167-277 (1981) and Langer, Chem. Tech. 12:98-105 (1982) or poly(vinylalcohol)), polylactides (U.S. Pat. No. 3,773,919, EP 58,481), copolymers of L-glutamic acid and gamma ethyl-L-glutamate (Sidman et al., Biopolymers 22:547-556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988). Each of these references is incorporated herein by reference in its entirety.

Sustained-release compositions also include liposomally entrapped agents. Liposomes containing the agents described herein are prepared by methods known per se: DE 3,218,121; Epstein et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324, each of which is incorporated herein by reference. Ordinarily the liposomes are of the small (about 200-800 Angstroms) unilamellar type in which the lipid content is greater than about 30 mol. % cholesterol, the selected proportion being adjusted for the optimal therapy.

Other similar delivery methods, such as via nanocapsules, microparticles, microspheres, nanoparticles, lipid particles, vesicles, and the like are contemplated. Typically, the agents may be formulated for delivery either encapsulated in a lipid particle, a liposome, a vesicle, a nanosphere, or a nanoparticle for example, and may further include a targeting molecule exposed to aid in site-specific delivery of the agent.

The formation and use of liposomes is generally known to those of skill in the art (see for example, Couvreur et al., FEBS Lett. 1977 Dec. 15; 84(2):323-6; Couvreur, Crit Rev Ther Drug Carrier Syst. 1988; 5(1):1-20; Lasic, Trends Biotechnol. 1998 July; 16(7):307-21; Gabizon & Papahadjopoulos, Proc Natl Acad Sci USA. 1988 September; 85(18): 6949-53; Allen and Chonn, FEBS Lett. 1987 Oct. 19; 223(1):42-6; U.S. Pat. No. 5,741,516, which are incorporated by reference herein in their entirety). Further, various methods of liposome and liposome like preparations as potential drug carriers have been reviewed (Takakura, Nippon Rinsho, 1998 March; 56(3):691-5; Chandran et al., Indian J Exp Biol. 1997 August; 35(8):801-9; Margalit, Crit Rev Ther Drug Carrier Syst. 1995; 12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each of which is incorporated herein by reference in its entirety).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the agents. They are widely suitable as both water- and lipid-soluble substances can be entrapped, i.e. in the aqueous spaces and within the bilayer itself, respectively.

In addition to the teachings of Couvreur et al. FEBS Lett. 1977 Dec. 15; 84(2):323-6; and Couvreur et al., Crit Rev Ther Drug Carrier Syst. 1988; 5(1):1-20, the following information may be utilized in generating liposomal formulations. Phospholipids can form a variety of structures other than liposomes when dispersed in water, depending on the molar ratio of lipid to water. At low ratios the liposome is the typical structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most typical liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Alternatively, pharmaceutically-acceptable nanocapsule formulations may be used to entrap the agents in a stable and reproducible way (Henry-Michelland et al., J Pharm Pharmacology. 1987 December; 39(12):973-7; Quintanar-Guerrero et al., Drug Dev Ind Pharm. 1998 December; 24(12): 1113-28; Douglas et al., Crit Rev Ther Drug Carrier Syst. 1987; 3(3):233-61, each of which is incorporated by reference herein in its entirety). To avoid side effects due to intracellular polymeric overloading, such ultrafine particles (sized around 0.1 µm) should be designed using polymers able to be degraded in vivo. For example, biodegradable polyalkyl-cyanoacrylate nanoparticles that meet these requirements are contemplated for use in the present invention. Such particles may be easily made, as described (Couvreur et al., 1980 supra and 1988, supra; zur Muhlen et al., Eur J Pharm Biopharm. 1998 March; 45(2):149-55; Zambaux et al. J Control Release. 1998 Jan. 2; 50(1-3):31-40; Pinto-Alphandry et al., 1995 J Drug Target. 1995; 3(2):167-9 and U.S. Pat. No. 5,145,684, each of which is incorporated herein by reference in its entirety).

The therapeutically effective dose of the agents will, of course, vary depending on such factors as the specific agent in question, the pathological condition to be treated (including prevention), the method of administration, any co-therapy involved, the subject's age, weight, general medical condition, medical history, etc., and its determination is well within the skill of a practicing physician. Accordingly, it may be necessary for the clinician to titer the dosage and modify the route of administration as required to obtain the maximal therapeutic effect. The clinician will administer the agent until a dosage is reached that achieves the desired effect for treatment of the condition in question. For example, if the objective is the treatment of sepsis, the amount would be, in one aspect, one that improves the septic condition.

With the above guidelines, the effective dose generally is within the range of from about 1.2 to about 24 mg/kg, more typically from about 2.4 to about 24 mg/kg, and most typically from about 2.4 to about 4 mg/kg.

For non-oral use, agents may be administered in the form of an injection at about 2 to 24 mg, typically about 2.4 to about 24 mg, most typically about 2.4 to about 4 mg, per kg body weight, 1 to 2 times daily by intravenous injection. It should be appreciated that endotoxin contamination should be kept minimally at a safe level, for example, less than about 0.5 ng/mg protein. Moreover, for human administration, the formulations generally meet sterility, pyrogenicity, general safety, and purity as required by the FDA Office and Biologics standards.

Certain factors may influence the dosage required to effectively treat a subject, including but not limited to the severity of the disease or disorder, previous treatments, the general health and/or age of the subject, and other diseases present. It will also be appreciated that the effective dosage of the agent used for treatment may increase or decrease over the course of a particular treatment. Changes in dosage may result and become apparent from the results of diagnostic assays. For example, the subject can be monitored after administering an agent described herein. Based on information from the monitoring, an additional amount of the agent can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on $EC_{50}$s found to be effective in in vitro and in vivo animal models.

Dosage levels on the order of about 1 µg/kg to 100 mg/kg of body weight per administration are useful in the treatment of a disease. One skilled in the art can also readily determine an appropriate dosage regimen for administering the disclosed to a given subject. For example, an agent described herein can be administered to the subject once, e.g., as a single injection. Alternatively, the agent can be administered once or twice daily to a subject for a period of from about three to about twenty-eight days, or from about seven to about ten days.

Thus, the agent can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of agent per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of agent per kg of bodyweight.

Delivery of an agent described herein such as an antagomir directly to an organ (e.g., directly to the liver) can be at a dosage on the order of about 0.00001 mg to about 3 mg per organ, or typically about 0.0001-0.001 mg per organ, about 0.03-3.0 mg per organ, about 0.1-3.0 mg per organ or about 0.3-3.0 mg per organ.

Where a dosage regimen comprises multiple administrations, it is understood that the effective amount of agent administered to the subject can include the total amount of agent administered over the entire dosage regimen. One skilled in the art will appreciate that the exact individual dosages may be adjusted somewhat depending on a variety of factors, including the specific agent being administered, the time of administration, the route of administration, the nature of the formulation, the rate of excretion, the particular disorder being treated, the severity of the disorder, the pharmacodynamics of the oligonucleotide agent, and the age, sex, weight, and general health of the patient. Wide variations in the necessary dosage level are to be expected in view of the differing efficiencies of the various routes of administration. For instance, oral administration would require higher dosage levels than administration by intravenous injection. Variations in these dosage levels can be adjusted using standard empirical routines of optimization, which are well-known in the art. The precise therapeutically effective dosage levels and patterns are typically determined by the attending physician in consideration of the above-identified factors. In one aspect, the unit dose is administered less frequently than once a day, e.g., less than every 2, 4, 8 or 30 days. In another aspect, the unit dose is not administered with a frequency (e.g., not a regular frequency). For example, the unit dose may be administered a single time. Because oligonucleotide agent-mediated silencing can persist for several days after administering the antagomir composition, in many instances, it is possible to administer the composition with a frequency of less than once per day, or, for some instances, only once for the entire therapeutic regimen.

In some aspects, a subject is administered an initial dose, and one or more maintenance doses of an agent described herein. The maintenance dose or doses are generally lower than the initial dose, e.g., one-half less of the initial dose. A maintenance regimen can include treating the subject with a dose or doses ranging from 0.01 g to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are typically administered no more than once every 5, 10, or 30 days. Further, the treatment regimen may last for a period of time which will vary depending upon the nature of the particular disease, its severity and the overall condition of the patient. In typical aspects, the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. Following successful treatment, it may be desirable to have the patient undergo maintenance therapy to prevent the recurrence of the disease state, wherein the compound of the invention is administered in maintenance doses, ranging from 0.01 µg to 100 g per kg of body weight.

In addition to treating pre-existing diseases or disorders, the agent described herein can be administered prophylactically in order to prevent or slow the onset of a particular disease or disorder. In prophylactic applications, an antagomir is administered to a patient susceptible to or otherwise at risk of a particular disorder, such as disorder associated with aberrant or unwanted expression of an miRNA of interest.

The route of administration is in accord with known methods, e.g., by injection or infusion by intravenous, intramuscular, intracerebral, intraperitoneal, intracerebrospinal, subcutaneous, intraocular, intraarticular, intrasynovial, intrathecal, oral, topical, or inhalation routes, or by sustained-release systems.

The effectiveness of an agent in preventing or treating the disorder in question may be improved by administering the agent serially or in combination with another pharmacological agent that is effective for analogous purposes, either in the same composition or as separate compositions.

For example, agents used to treat sepsis may be combined with antibiotic therapies and may act synergistically or additively with such other therapies. The effective amounts of the therapeutic agents administered in combination with the agents described herein will be at the physician's or veterinarian's discretion. Dosage administration and adjustment is done to achieve maximal management of the conditions to be treated. The dose will additionally depend on such factors as the type of the therapeutic agent to be used and the specific patient being treated. Typically, the amount employed will be the same dose as that used, if the given therapeutic agent is administered without the agents described herein.

The agents described herein can be formulated in combination with another agent, such as an agent that stabilizes an oligonucleotide agent, e.g., a protein that complexes with the oligonucleotide agent. Still other agents include chelators, e.g., EDTA (e.g., to remove divalent cations such as $Mg^{2+}$), salts, and RNAse inhibitors (e.g., a broad specificity RNAse inhibitor such as RNAsin).

In one aspect, when the agent is an antagomir, the antagomir preparation includes another antagomir, e.g., a second antagomir that can down-regulate expression of a second miRNA. In some aspects, the agents are directed to the same target nucleic acid but different target sequences. In another aspect, each antagomir is directed to a different target.

A compound can be formulated in combination with one or more other compounds, especially other compounds involved in inhibition of cholesterol synthesis or uptake, such as a statin, bile acid sequestrants, cholesterol absorption inhibitors such as fibrate, nicotinic acid, etc.

Methods of Treatment Using the miRNA Inhibitory Agents

Agents that have activity in the in vivo and/or in vitro assays described herein are likely to have therapeutic uses in a variety of disorders associated with sepsis, inflammation, organ protection, microvasculature function, and/or apoptosis.

Sepsis and subsequent multiple organ failure remain the major cause of morbidity and mortality in intensive care units. Sepsis represents a patient's response to a severe infection. Components of the Gram-negative bacterial cell wall (endotoxins or lipopolysaccharides) are the predominant species responsible for the initiation of sepsis. The patho-physiology of sepsis is due to the inappropriate regulation of the response to eradicate pathogens. Under normal conditions, the first pathogen contact with the inflammatory system will eliminate the infection with microbe and quickly return the host to homeostasis. In sepsis, the inflammatory system is often over-activated thereby accelerating the response to infection. Rapid lymphocyte apoptosis, delayed apoptosis of neutrophils, and enhanced apoptosis and necrosis of cells/tissues all contribute to the pathogenesis of sepsis and multiple organ failure. Thus, abrogation of apoptosis protects organs and represents a potential therapeutic strategy for sepsis and its associated multiple organ failure. As such, inhibition of the miR-15 family may up-regulate anti-apoptotic proteins (and/or prevent down-regulation of apoptotic proteins) and thereby protect organs against sepsis-induced apoptotic cell death.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Materials and Methods
1. Materials

Primary Human Umbilical Vein Endothelial Cells were purchased from Invitrogen and cultured following the manufacturer's instruction. Lipopolysaccharide (LPS) was purchased from Sigma.

2. Transfection

A chemically modified antisense oligonucleotide (antagomir, GenePharm Co. Ltd) and a synthetic miR-195 mimic (Qiagen) were used to inhibit and over-express miR-195 expression, respectively. A scrambled oligonucleotide (GenePharm Co. Ltd) was used as a control. Transfection was performed on Human Umbilical Vein Endothelial Cells by using TransMessenger transfection reagent (Qiagen) according to the manufacturer's instructions.

3. Caspase-3 Activity

As described in detail previously, caspase-3 activity was measured by using a caspase-3 fluorescent assay kit (BIOMOL Research Laboratories). Briefly, tissues or cultured cells were homogenized, and protein concentration was determined using the Bradford method. Samples (200-400 µg protein) in duplicates were incubated with caspase-3 substrate Ac-DEVD-AMC or Ac-DEVD-AMC plus inhibitor AC-DEVD-CHO at 37° C. for 2 hours before measurements were made by a fluorescent spectrophotometer (excitation at 380 nm, emission at 405 nm). Signals from inhibitor-treated samples served as background.

4. Measurement of Cellular DNA Fragmentation

Cells were pre-labelled with BrdU and then incubated with palmitate. DNA fragmentation was measured using a Cellular DNA Fragmentation ELISA kit (Roche Applied Science) according to the manufacturer's instructions.

5. In Situ Detection of Apoptotic Cells

To localize cells undergoing nuclear DNA fragmentation in tissues, in situ terminal deoxynucleotidyl transferase-mediated dUTP nick-end labeling (TUNEL) was performed using an in situ apoptosis detection kit (Roche Biochemicals) as described previously.

6. Determination of Liver Damage

Alanine aminotransferase (ALT) and aspartate aminotransferase (AST) were measured as indicators of the damage to liver using assay kits from BioAssay Systems according to the manufacturer's instructions.

7. Assessment of Renal Function

Blood urea nitrogen was determined using urea nitrogen detection kit according to the manufacturer's instructions.

8. MPO Activity

As an index of neutrophils infiltration, myeloperoxidase (MPO) activity in the tissue was determined. Briefly, the tissues were excised, placed in phosphate buffer, and homogenized. A 1:10 dilution of the homogenate (10% wt/vol) was centrifuged at 6000 g for 20 min at 4-8° C. The pellet was re-homogenized and sonicated for 10 s in 1 ml of 50 mM acetic acid (pH 6.0) containing 0.5% CETOH detergent. The prepared samples were used in reactions for MPO activity determined spectrophotometrically (650 nm) by measuring hydrogen peroxide-dependent oxidation of 3.3V, 5.5V-tetramethylbenzidine.

9. Real-Time RT-PCR for TNF-Alpha and iNOS mRNA Expression

Total RNA was extracted from fresh or frozen tissues using the Trizol Reagent (Gibco-BRL) following the manufacturer's instructions. Real-time RT-PCR for mouse TNF-α, iNOS and glyceraldehyde-3-phosphate dehydrogenase (GAPDH) mRNA was performed. The primers for TNF-α, iNOS and GAPDH were described previously.

10. Mouse Model of LPS-Induced Sepsis

Adult male mice (C57BL/6, aged 2 months) received LPS (4 mg/kg, i.p.). At different time points (6, 12 and 30 hours) after LPS treatment, mice were killed and tissues collected.

11. Mouse Model of Feces-in Peritoneum-Induced Sepsis

Sepsis was induced in adult male C57BL/6 mice (2 months old) by faeces injection into peritoneum as described previously. Faeces were collected from the cecum of a donor mouse, mixed with sterile saline at concentration of up to 75 mg/ml, and then injected intraperitoneally at 50 ml/kg. Control mice were injected intraperitoneally with sterile saline (50 ml/kg).

12. Delivery of DNA Plasmid and Oligonucleotides

Plasmid DNA (60 µg) or oligonucleotides (600 µg) was mixed with 40 µl of transfection reagent NANOPARTICLE (Altogen Biosystems, Las Vegas, Nev., USA) with total volume of 500 µl of 5% glucose (W/V), as per the manufacturer's instruction. The mixture was intravenously injected into the C57/BL6 mouse via the tail vein.

The miRZip shRNA for knocking down miR-195 (miR-Zip™ anti-sense microRNA-195) was provided by System Biosciences. An empty miRZip shRNA plasmid was used as a control.

The sequence for miR-195 antisense (miRZip-195) was: 5' GCCAATATTTCTGTGCTGCTA 3', and a mismatched sequence (miRZip000) served as a control: 5' GTTAACAC-CCTCGCGTCGTCA 3'.

13. Assessment of Micro-Vascular Dysfunction

Intravital video microscopy was used to analyze microvascular dysfunction. We utilized the extensor digitorum longus (EDL) muscle in mice anesthetized with ketamine and xylazine. Animals were kept warm with a heating lamp. The muscle was used as a "bioassay" accessible to intravital microscopy as other organs are difficult to study with this technique, mainly because of the organ's physical movement and technical problems with transillumination. Regarding sepsis-induced microvascular dysfunction, the muscle shows a typical capillary flow impairment that is seen in septic patients.

To assess capillary blood flow stoppage at the muscle surface, the muscle was epi-illuminated with bright light, blood flow in the capillary bed was visualized and videorecorded, and the density of capillaries with moving red blood cells and stationary red blood cells was measured from the recordings. The percentage of stopped-flow capillaries was computed from these measurements as described previously.

14. Statistical Analysis

All data were given as MEAN±SD. Differences between 2 groups were compared by unpaired Student t test. ANOVA followed by Newman-Keuls test was performed for multigroup comparisons. A value of $P<0.05$ was considered statistically significant.

Figure 1B:
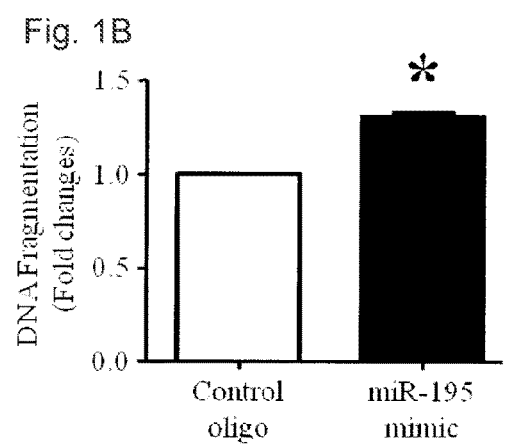

Example 1—Up-Regulation of microRNA-195 is Sufficient to Induce Apoptosis in Endothelial Cells Apoptotic endothelial cell death contributes to endothelial dysfunction in sepsis. To determine whether up-regulation of miR-15 family induces apoptosis in endothelial cells, we transfected endothelial cells with microRNA-195 (miR-195) mimic or control oligo. Twenty-four hours later, apoptosis was determined by caspase-3 activity (FIG. 1A) and DNA fragmentation (FIG. 1B). These results suggest that upregulation of miR-195 significantly induces apoptosis in endothelial cells. Thus, it is possible that elevation of miR-15 family members in blood promotes endothelial cell apoptotic death, leading to endothelial dysfunction in sepsis.

Figure 2A:
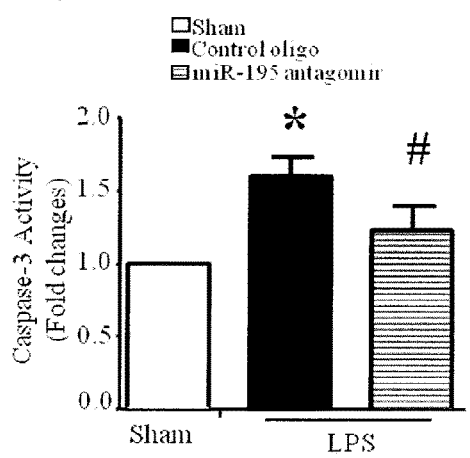
FIGS. 2A and 2B show that inhibition of miR-195 reduces lipopolysaccharide-induced apoptosis in endothelial cells.
Figure 2B:
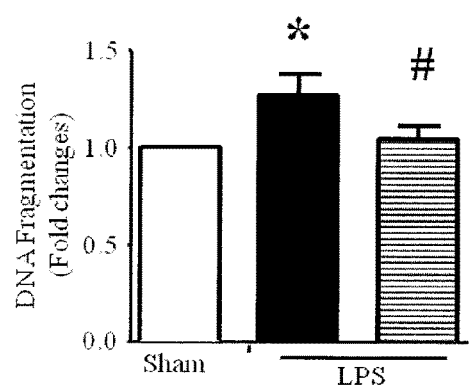

Example 2—Inhibition of miR-195 Reduces Lipopolysaccharide-Induced Apoptosis in Endothelial Cells If up-regulation of the miR-15 family contributes to apoptosis, inhibition of miR-15 family will provide a protective effect in endothelial cells under septic conditions. To this end, endothelial cells were transfected with miR-195 antagomir or control oligo, and then incubated with lipopolysaccharide (LPS) or saline as sham. Twenty-four hours later, apoptosis was determined. LPS induced apoptosis was significantly reduced by inhibition of miR-195 with its antagomir, as reflected by caspase-3 activity (FIG. 2A) and DNA fragmentation (FIG. 2B). These results support the view that inhibition of miR-15 family prevents apoptosis in endothelial cells under septic conditions and thus protects vasculature in sepsis.

Figure 4:
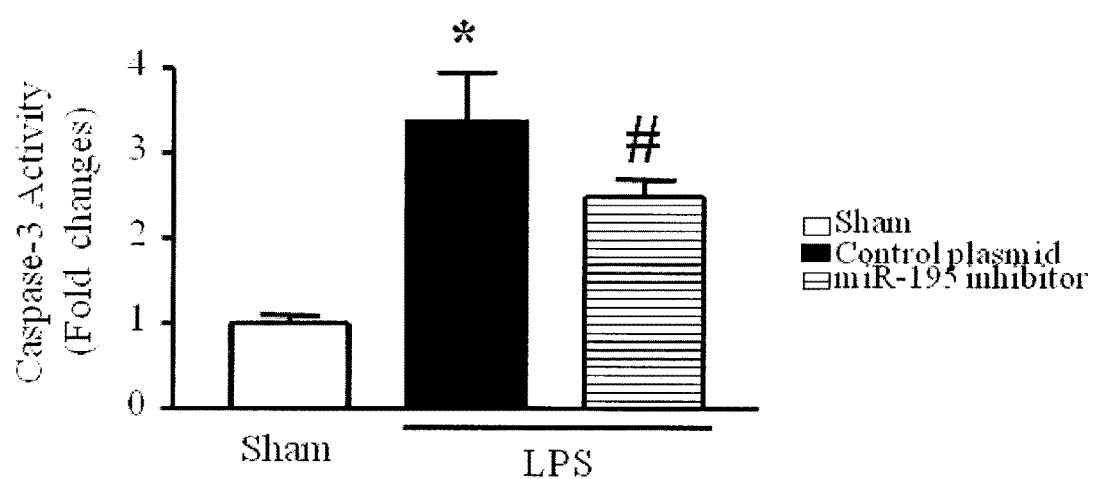
FIG. 4 shows the effects of miR-195 inhibition on apoptosis in lung tissues in a mouse model of LPS-induced sepsis.
Figure 5A:
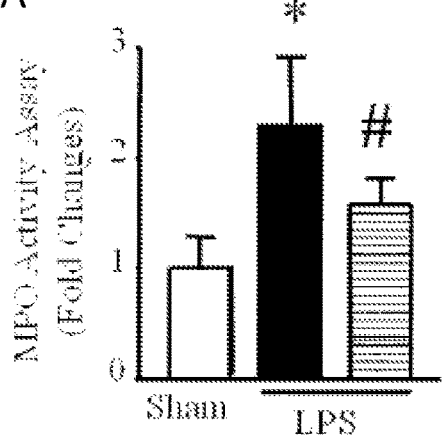
FIGS. 5A, 5B, and 5C show the effects of miR-195 inhibition on inflammatory responses in liver tissues in a mouse model of LPS-induced sepsis.
Figure 5B:
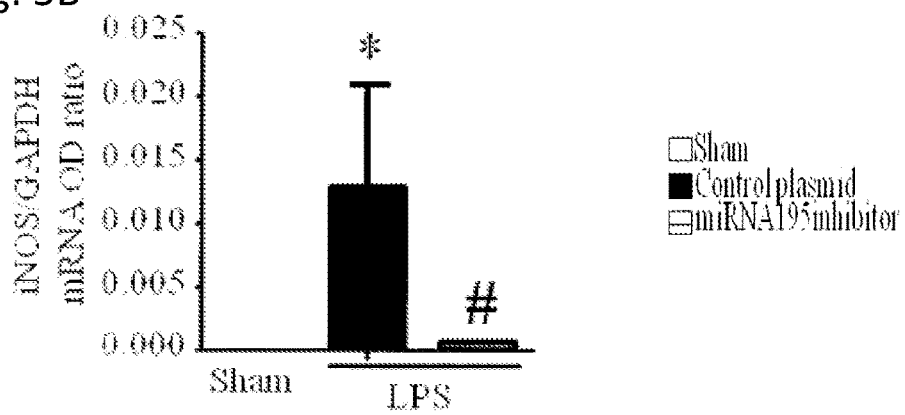
Figure 5C:
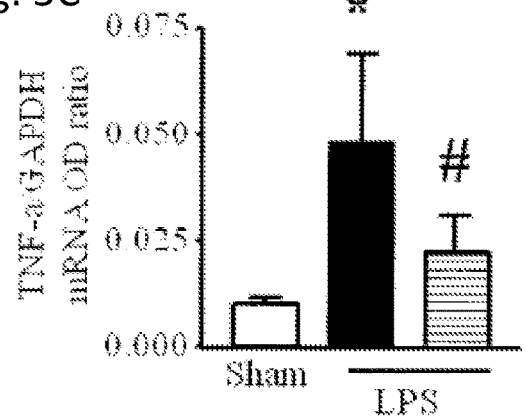
Figure 6:
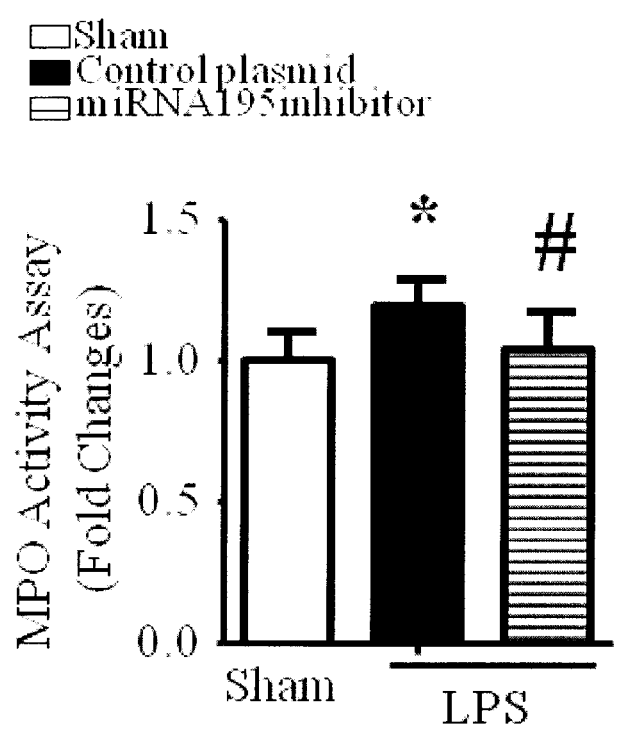
FIG. 6 shows the effects of miR-195 inhibition on inflammatory responses in kidney tissues in a mouse model of LPS-induced sepsis.
Figure 7A:
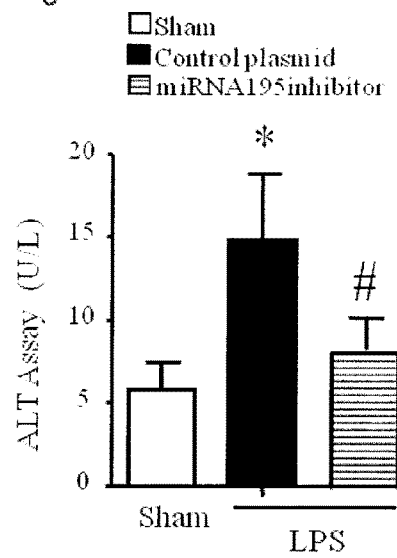
FIGS. 7A, 7B, and 7C show the effects of miR-195 inhibition on organ dysfunction in a mouse model of LPS-induced sepsis.
Figure 7B:
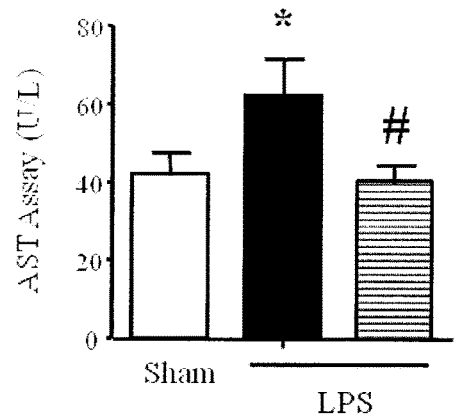
Figure 7C:
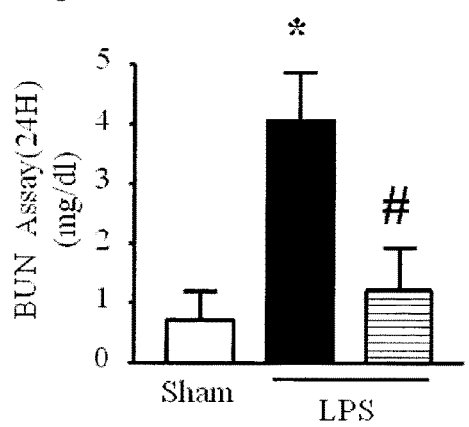
Figure 8A:
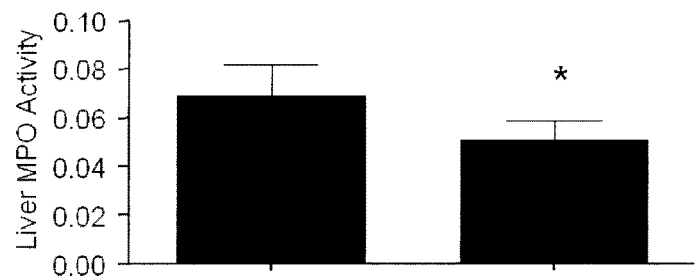
FIGS. 8A, 8B, 8C, and 8D show the effects of miR-195 inhibition on apoptosis and inflammation in the liver of a mouse model of feces-in peritoneum-induced sepsis.
Figure 8B:
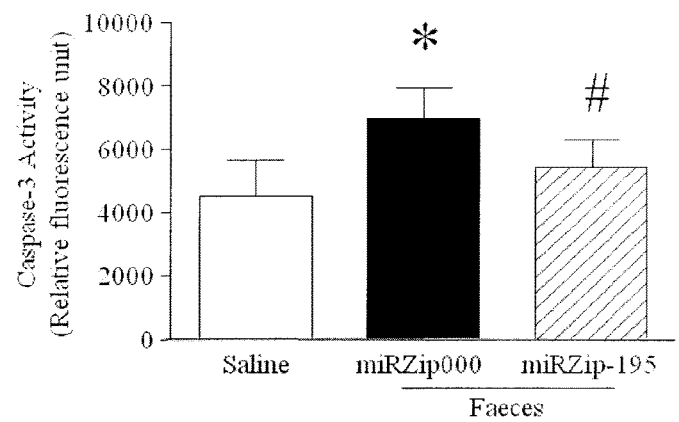
Figure 8C:
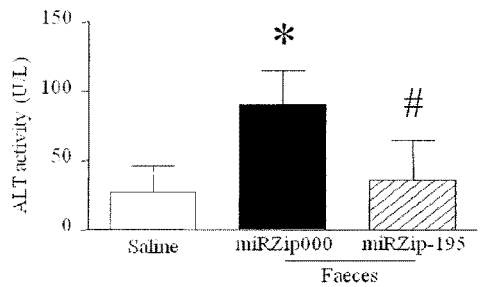
Figure 8D:
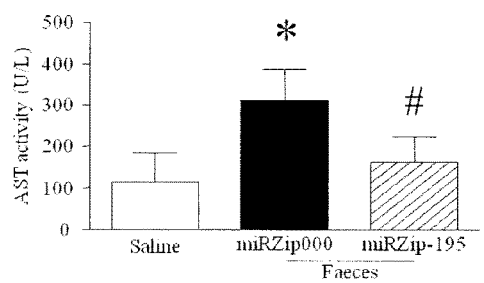
Figure 9A:
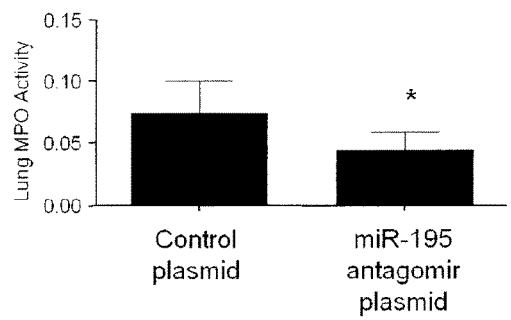
FIGS. 9A, 9B, 9C, 9D, and 9E show the effects of miR-195 inhibition on apoptosis and inflammation in the lungs of a mouse model of feces-in peritoneum-induced sepsis.
Figure 9B:
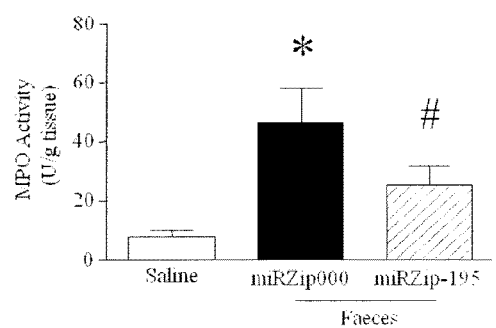
Figure 9C:
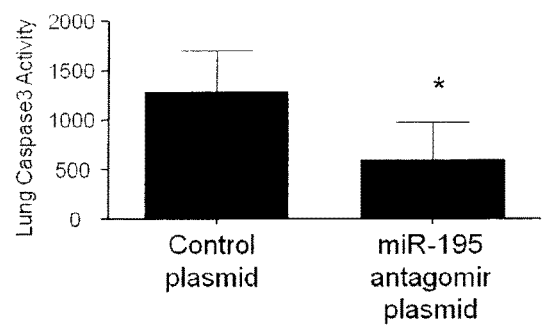
Figure 9D:
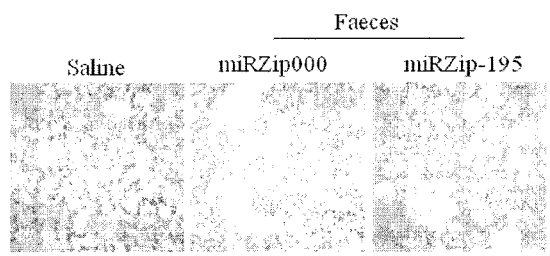
Figure 9E:
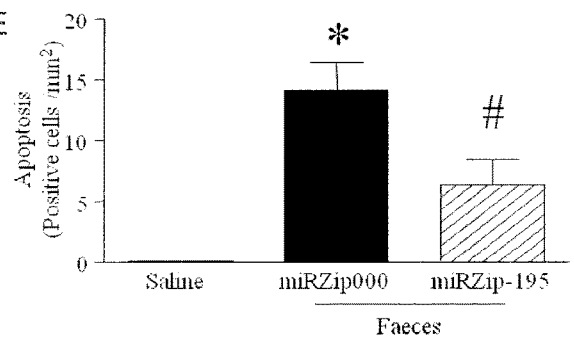

Example 3—Effects of miR-195 Inhibition on Apoptosis, Inflammation and Organ Dysfunction in a Mouse Model of LPS-Induced Sepsis To study the in vivo significance of miR-195 inhibition in sepsis, we injected adult mice with a plasmid expressing miR-195 antagomir or an empty plasmid as a control (80 μg/mouse, i.v.) in combination with a nano-particle transfection reagent. Systemic injection of the plasmid expressing miR-195 antagomir inhibits miR-195 expression in mice. Forty-eight hours later, mice received LPS (4 mg/kg, i.p.) or saline. Twenty-four hours after LPS injection, tissues from liver, lung and kidney were collected. Apoptosis was measured in liver tissues (FIGS. 3A, 3B, and 3C) and lung tissues (FIG. 4); inflammatory responses were measured in liver tissues (FIGS. 5A, 5B, and 5C) and kidney tissues (FIG. 6); and organ dysfunction was measured (FIGS. 7A, 7B, and 7C).

Figure 3A:
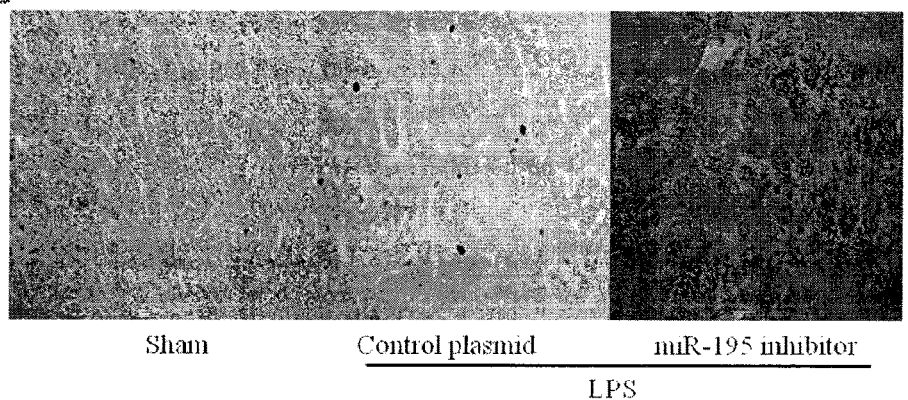
FIGS. 3A, 3B, and 3C show the effects of miR-195 inhibition on apoptosis in liver tissues in a mouse model of LPS-induced sepsis.
Figure 3B:
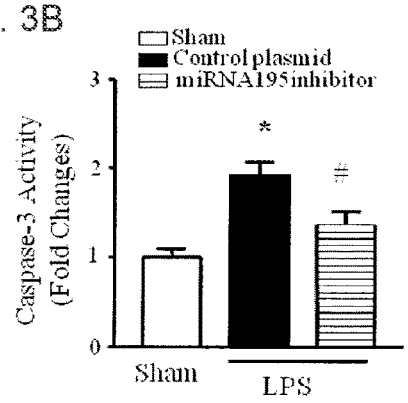
Figure 3C:
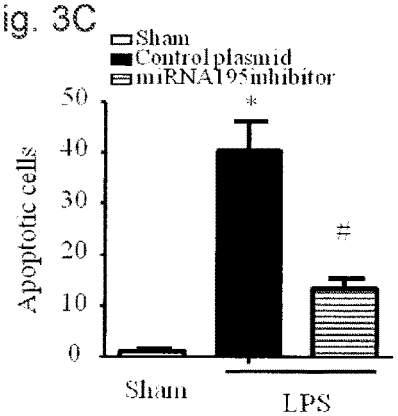

Inhibition of miR-195 decreased caspase-3 activation in liver (FIG. 3B) and lung (FIG. 4) induced by LPS. The inhibitory effect of miR-195 inhibition on apoptosis was further confirmed by TUNEL staining in liver (FIGS. 3A and C). Inhibition of miR-195 also significantly attenuated MPO activity, an indicator of neutrophil infiltration in liver (FIG. 5A) and kidney (FIG. 6), iNOS (FIG. 5B) and TNF-alpha expression in liver (FIG. 5C), suggesting suppression of inflammatory responses in endotoxemic mice. Consequently, ALT activity (FIG. 7A) and AST activity (FIG. 7B), indicators of liver injury, were decreased and BUN levels, indicator of renal dysfunction, were also decreased after miR-195 inhibition in endotoxemic mice. These results indicate that inhibition of miR-195 reduces apoptosis, inflammation and organ injuries in a mouse model of LPS induced sepsis.

Example 4—Effects of miR-195 Inhibition on Apoptosis and Inflammation in a Mouse Model of Feces-in Peritoneum-Induced Sepsis To further assess the role of miR-195 in sepsis, we used a more clinically relevant mouse model of feces-in-peritoneum induced sepsis. To this end, adult mice were injected with a plasmid expressing miR-195 antagomir or an empty plasmid as a control (80 μg/mouse, i.v.) in combination with a nano-particle transfection reagent. Forty-eight hours later, adult mice were injected with feces (75 mg/kg, i.p.) or saline as sham. Eight hours after feces infection, apoptosis and inflammation were determined in liver (FIG. 8) and lung (FIG. 9).

Figure 10:
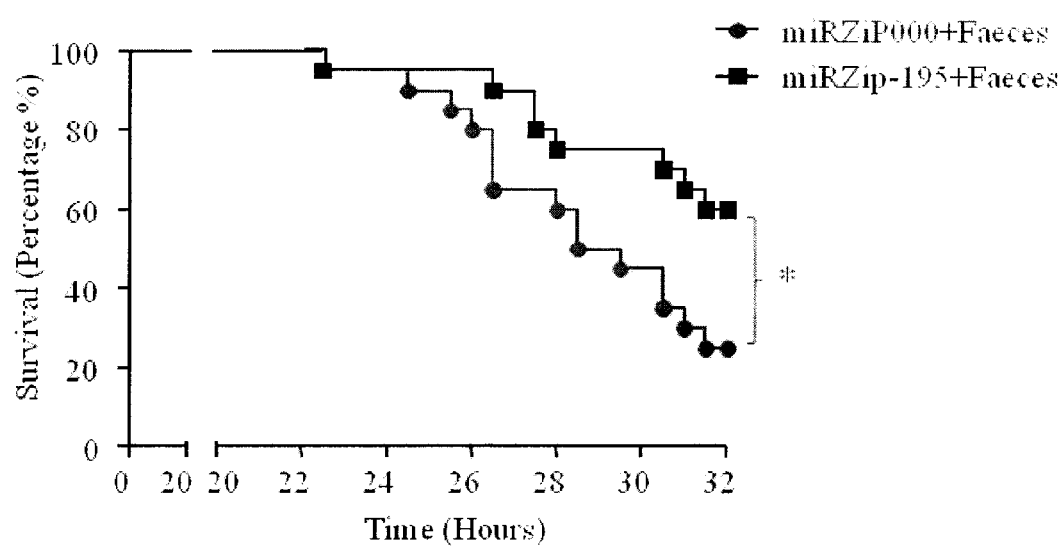
FIG. 10 shows the effects of miR-195 inhibition on survival in a mouse model of feces-in peritoneum-induced sepsis.

As shown in FIG. 8, inhibition of miR-195 significantly decreased MPO activity (FIG. 8A), caspase-3 activity (FIG. 8B), ALT activity (FIG. 8C), and AST activity (FIG. 8D) in the liver of feces-injected mice. As shown in FIG. 9, inhibition of miR-195 significantly decreased MPO activity (FIGS. 9A and 9B), caspase-3 activity (FIG. 9C), and apoptosis (FIGS. 9D and 9E) in the lungs of feces-injected mice. As shown in FIG. 10, inhibition of miR-195 significantly increased survival in these mice.

Thus, inhibition of miR-195 reduces apoptosis and inflammation, as well as lung and liver injury, while increasing survival in a more clinical relevant mouse model of feces-in-peritoneum induced sepsis, further supporting the protective effects of miR-195 inhibition on sepsis.

Example 5—Therapeutic Effects of miR-195 Inhibition on Apoptosis, Inflammation and Organ Dysfunction in a Mouse Model of LPS-Induced Sepsis In the above studies, miR-195 was inhibited first and then sepsis was induced in mice. Thus, these studies have demonstrated that inhibition of miR-195 prevents apoptosis, inflammatory responses and organ injuries in sepsis. In this study, the therapeutic effects of miR-195 inhibition in sepsis were examined. Adult mice were injected with LPS (4 mg/kg, i.p.) and within 30 minutes after LPS injection, the animals were administrated with synthesized miR-195 antisense oligo or a control oligo (600 μg, i.v.). Thirty hours later, apoptosis, inflammation and renal function were assessed (FIGS. 11A, 11B, 11O, 11D, 11E, and 11F).

Figure 11A:
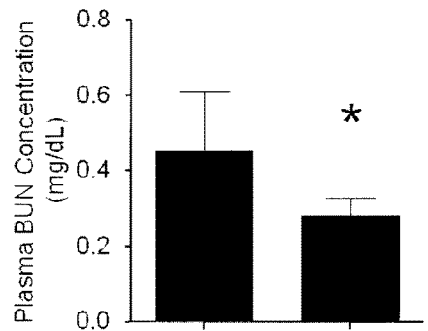
Figure 11B:
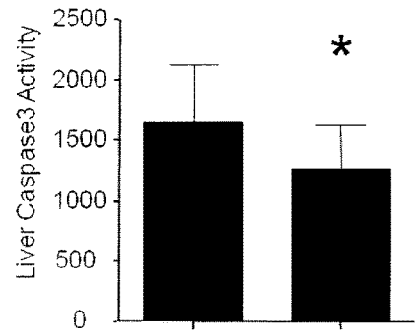
Figure 11C:
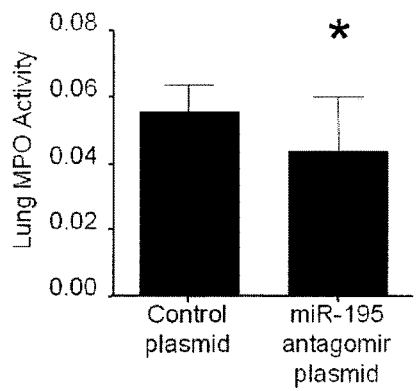
Figure 11D:
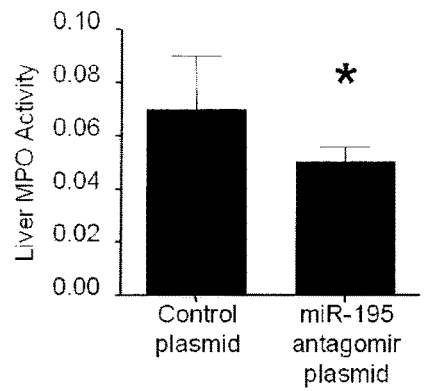
Figure 11E:
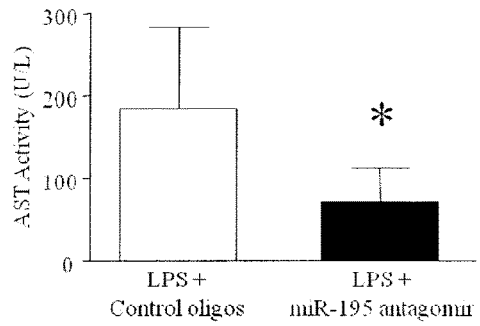
Figure 11F:
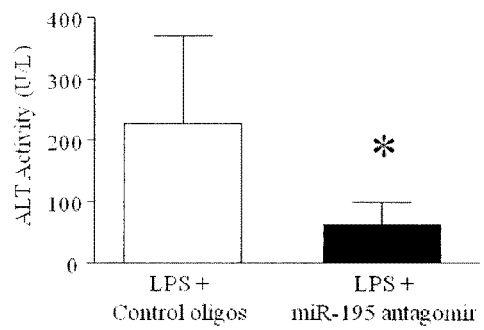

Administration of miR-195 antisense oligo lowered BUN levels, indicative of attenuation of renal dysfunction (FIG. 11A), decreased caspase-3 activity in liver, indicative of inhibition of apoptosis (FIG. 11B), and reduced MPO activity in lung (FIG. 11C) and liver (FIG. 11D), indicative of a reduction in inflammatory cell infiltrations in sepsis. Additionally, administration of the miR-195 antisense oligo reduced AST activity (FIG. 11E) and ALT activity (FIG. 11F), indicating a reduction in sepsis-induced liver injury. These results demonstrate the therapeutic effects of miR-195 inhibition in sepsis.

Figure 12:
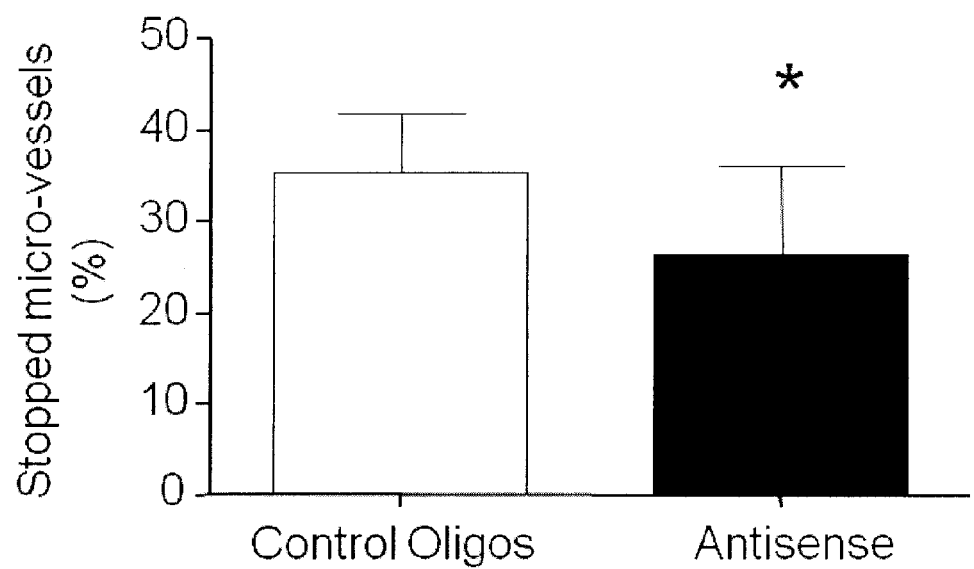
FIG. 12 shows the therapeutic effects of miR-195 inhibition on microvascular dysfunction in a mouse model of LPS-induced sepsis.

Example 6—Therapeutic Effects of miR-195 Inhibition on Microvascular Dysfunction in a Mouse Model of LPS-Induced Sepsis Adult mice were injected with LPS (4 mg/kg, i.p.) and within 30 minutes after LPS injection, the animals were administrated with synthesized miR-195 antisense oligo or a control oligo (600 μg, i.v.). Thirty hours later, microvascular dysfunction was assessed (FIG. 12). Consistently, administration of miR-195 antisense oligo attenuated microvascular dysfunction in sepsis.

The above disclosure generally describes the present invention. Although specific terms have been employed herein, such terms are intended in a descriptive sense and not for purposes of limitation.

All publications, patents and patent applications are herein incorporated by reference in their entirety to the same extent as if each individual publication, patent or patent application was specifically and individually indicated to be incorporated by reference in its entirety.

Although exemplary aspects of the invention have been described herein in detail, it will be understood by those skilled in the art that variations may be made thereto without departing from the spirit of the invention or the scope of the appended claims.

What is claimed is:

1. A method of treating sepsis in a subject comprising administering to the subject an agent that inhibits the activity of miR-195 that is upregulated in sepsis, wherein sepsis in the subject is reduced.

2. The method of claim 1, wherein an organ function selected from the group consisting of liver function, lung function, kidney function, and microvasculature function is protected.

3. The method of claim 1, wherein apoptosis in at least one of endothelial cells, liver cells, kidney cells, and immune cells is reduced.

4. The method of claim 3, wherein the immune cells are macrophages.

5. The method of claim 1, wherein an inflammatory response in at least one of a liver, lung, kidney, and microvasculature is reduced.

6. The method of claim 1, wherein the sepsis is lipopolysaccharide-induced sepsis or feces-induced sepsis.

7. The method of claim 1, wherein the agent is a locked nucleic acid (LNA) oligomer, a Morpholino oligomer, a 2'-O-methyl RNA oligomer, an antagomir, a steric-blocking oligomer that inhibits miRNA maturation, or a steric-blocking oligomer that blocks the miRNA-195 target site of an mRNA transcript.

* * * * *